(12) United States Patent
Thor

(10) Patent No.: US 11,857,448 B2
(45) Date of Patent: Jan. 2, 2024

(54) METHODS AND APPARATUS FOR TREATING OSTEOARTHRITIS OF THE KNEE

(71) Applicant: OTTO BOCK HEALTHCARE, LP, Minneapolis, MN (US)

(72) Inventor: Arni Thor, San Diego, CA (US)

(73) Assignee: OTTO BOCK HEALTHCARE LP, Austin, TX (US)

( * ) Notice: Subject to any disclaimer, the term of this patent is extended or adjusted under 35 U.S.C. 154(b) by 1158 days.

(21) Appl. No.: 16/265,874

(22) Filed: Feb. 1, 2019

(65) Prior Publication Data

US 2019/0240056 A1 Aug. 8, 2019

Related U.S. Application Data

(63) Continuation-in-part of application No. 15/977,880, filed on May 11, 2018, now Pat. No. 11,484,426.
(Continued)

(51) Int. Cl.
*A61F 5/01* (2006.01)

(52) U.S. Cl.
CPC .......... *A61F 5/0125* (2013.01); *A61F 5/0123* (2013.01); *A61F 5/0106* (2013.01);
(Continued)

(58) Field of Classification Search
CPC .... A61F 5/0106; A61F 5/0109; A61F 5/0123; A61F 5/0125; A61F 2005/0139; A61F 2005/0146

See application file for complete search history.

(56) References Cited

U.S. PATENT DOCUMENTS 2,949,111 A 8/1960 Ruotoistenmaki
4,646,726 A 3/1987 Westin et al.
(Continued)

FOREIGN PATENT DOCUMENTS

DE 102004019007 A1 11/2005
DE 102015116931 A1 4/2017
(Continued)

OTHER PUBLICATIONS

"International Search Report and Written Opinion of the International Searching Authority," issued in connection with Int'l Appl. No. PCT/US2018/032480, dated Aug. 10, 2018 (9 pages).
(Continued)

*Primary Examiner* — Keri J Nelson
(74) *Attorney, Agent, or Firm* — HOLLAND & HART LLP

(57) ABSTRACT

Methods and apparatus for an orthopedic device. In one embodiment, the orthopedic device includes a first panel defining opposed first and second sides; a second panel having a first end secured to the first side of the first panel along a seam, and a second end securable to the second side of the first panel at a location site; and a first strap having a first end secured to the first side of the first panel along the seam and laying under the second panel, and a second end securable to the second side of the first panel at the location site. The orthopedic device may include a dynamic force strap that includes three ends, that collectively helically extend between upper and lower portions of the orthopedic device and connect to the first panel.

5 Claims, 19 Drawing Sheets

Related U.S. Application Data

(60) Provisional application No. 62/625,893, filed on Feb. 2, 2018, provisional application No. 62/696,251, filed on Jul. 10, 2018.

(52) U.S. Cl.
CPC ..... *A61F 5/0109* (2013.01); *A61F 2005/0139* (2013.01); *A61F 2005/0146* (2013.01)

(56) References Cited

U.S. PATENT DOCUMENTS

| | | | |
|---|---|---|---|
| 4,776,326 A | | 10/1988 | Young |
| 4,805,606 A | * | 2/1989 | McDavid, III ........ A61F 5/0125 2/22 |
| 5,277,698 A | | 1/1994 | Taylor |
| 5,513,658 A | * | 5/1996 | Goseki ................. A61F 5/0109 128/882 |
| 5,562,605 A | | 10/1996 | Taylor |
| 5,776,090 A | | 7/1998 | Bergmann et al. |
| 5,817,041 A | | 10/1998 | Bader |
| 5,897,515 A | | 4/1999 | Willner et al. |
| 6,110,135 A | | 8/2000 | Madow et al. |
| 6,146,344 A | | 11/2000 | Bader |
| 6,146,349 A | | 11/2000 | Rothschild et al. |
| 6,383,156 B1 | * | 5/2002 | Enzerink ............... A61F 5/0125 602/26 |
| 6,676,618 B2 | | 1/2004 | Andersen |
| 6,945,947 B2 | | 9/2005 | Ingimundarson et al. |
| 7,077,818 B2 | | 7/2006 | Ingimundarson et al. |
| 7,198,610 B2 | | 4/2007 | Ingimundarson et al. |
| 7,266,910 B2 | | 9/2007 | Ingimundarson |
| 7,270,644 B2 | | 9/2007 | Ingimundarson |
| 7,513,880 B2 | | 4/2009 | Ingimundarson et al. |
| 7,749,423 B2 | | 7/2010 | Bader |
| 7,766,851 B2 | | 8/2010 | Lindh et al. |
| 8,021,316 B2 | | 9/2011 | Franke et al. |
| 8,323,224 B2 | | 12/2012 | Shlomovitz |
| 8,403,872 B2 | | 3/2013 | Franke et al. |
| 8,540,655 B2 | | 9/2013 | Franke et al. |
| 8,864,692 B2 | * | 10/2014 | Ingimundarson ..... A61F 5/0123 602/5 |
| 9,121,673 B2 | | 9/2015 | Popovici |
| 9,192,504 B2 | | 11/2015 | Andrews et al. |
| 9,211,208 B2 | | 12/2015 | Blum et al. |
| 9,326,880 B2 | | 5/2016 | Szczepanski et al. |
| 9,433,522 B2 | | 9/2016 | Bader |
| 9,562,742 B2 | | 2/2017 | Popovici |
| 9,889,035 B2 | | 2/2018 | Jordan et al. |
| 9,901,475 B2 | | 2/2018 | Jordan et al. |
| 9,980,847 B2 | | 5/2018 | Andrews et al. |
| 10,052,221 B2 | | 8/2018 | Albertsson et al. |
| 10,105,252 B2 | | 10/2018 | Bader |
| 10,561,514 B2 | | 2/2020 | Romo et al. |
| 2005/0020951 A1 | | 1/2005 | Gaylord et al. |
| 2005/0234378 A1 | | 10/2005 | Ingimundarson et al. |
| 2007/0038169 A1 | | 2/2007 | Alon et al. |
| 2007/0073202 A1 | | 3/2007 | Bader |
| 2007/0100268 A1 | | 5/2007 | Fisher |
| 2008/0077066 A1 | | 3/2008 | Lewis |
| 2008/0300525 A1 | | 12/2008 | Shlomovitz |
| 2009/0287128 A1 | | 11/2009 | Ingimundarson et al. |
| 2013/0072841 A1 | | 3/2013 | Bader |
| 2013/0131569 A1 | | 5/2013 | Blum et al. |
| 2013/0178772 A1 | | 7/2013 | Oaks et al. |
| 2014/0194801 A1 | | 7/2014 | Thorsteinsdottir et al. |
| 2014/0214016 A1 | | 7/2014 | Ingimundarson |
| 2014/0276318 A1 | | 9/2014 | Faux |
| 2014/0276320 A1 | | 9/2014 | Faux et al. |
| 2014/0378881 A1 | | 12/2014 | Wagner |
| 2015/0065934 A1 | | 3/2015 | Bader |
| 2015/0119781 A1 | | 4/2015 | Ponce |
| 2015/0148725 A1 | | 5/2015 | Johnsson et al. |
| 2015/0150709 A1 | | 6/2015 | Ljubimir et al. |
| 2015/0265450 A1 | | 9/2015 | Rodgers |
| 2015/0320581 A1 | | 11/2015 | Causse |
| 2016/0074199 A1 | | 3/2016 | Bader |
| 2016/0193066 A1 | | 7/2016 | Albertson |
| 2016/0213552 A1 | | 7/2016 | Lindsay |
| 2016/0220406 A1 | | 8/2016 | Bader |
| 2017/0165094 A1 | | 6/2017 | Voskuilen et al. |
| 2017/0165095 A1 | | 6/2017 | Romo et al. |
| 2017/0216071 A1 | | 8/2017 | Bader |
| 2017/0348132 A1 | | 12/2017 | Cooney |
| 2018/0333285 A1 | | 11/2018 | Thor et al. |

FOREIGN PATENT DOCUMENTS

| | | |
|---|---|---|
| EP | 0121725 A2 | 10/1984 |
| EP | 0270661 B1 | 1/1992 |
| EP | 2512387 B1 | 9/2015 |
| EP | 2932944 A1 | 10/2015 |
| EP | 3123986 A1 | 2/2017 |
| EP | 3301680 A1 | 4/2018 |
| GB | 2375962 A | 12/2002 |
| GB | 2535612 A | 8/2016 |
| GB | 2556317 A | 5/2018 |
| GB | 2571963 A | 9/2019 |
| GB | 2571965 A | 9/2019 |
| RU | 2277394 C2 | 6/2006 |
| WO | 01/34071 A1 | 5/2001 |
| WO | 2004/066890 A1 | 8/2004 |
| WO | 2008/001394 A2 | 1/2008 |
| WO | 2009/139019 A1 | 11/2009 |
| WO | 2011/029837 A1 | 3/2011 |
| WO | 2014/001793 A1 | 1/2014 |
| WO | 2017/103621 A1 | 6/2017 |
| WO | 2017/134429 A1 | 8/2017 |
| WO | 2017/207532 A1 | 12/2017 |
| WO | 2017/212242 A1 | 12/2017 |
| WO | 2019/175589 A1 | 9/2019 |
| WO | 2019/175592 A1 | 9/2019 |

OTHER PUBLICATIONS

"International Search Report and Written Opinion of the International Searching Authority," issued in connection with Int'l Appl. No. PCT/US2019/016535, dated Jun. 20, 2019 (12 pages).

"International Search Report and Written Opinion of the International Searching Authority," issued in connection with Int'l Appl. No. PCT/US2020/047228, dated Dec. 2, 2020 (12 pages).

Extended European Search Report for EP Application No. 18798710.2 dated Apr. 2, 2020.

International Search Report for PCT/US18/32480 dated Aug. 10, 2018.

\* cited by examiner

METHODS AND APPARATUS FOR TREATING OSTEOARTHRITIS OF THE KNEE

PRIORITY

This application is a continuation of part of, and claims the benefit of priority to co-owned and co-pending U.S. patent application Ser. No. 15/977,880 filed May 11, 2018 and entitled "Methods and Apparatus for Human Anatomical Orthoses", the contents of which being incorporated herein by reference in its entirety.

This application also claims the benefit of priority to co-owned U.S. Provisional Patent Application Ser. No. 62/696,251 filed Jul. 10, 2018 of the same title, the contents of which being incorporated herein by reference in its entirety.

This application also claims the benefit of priority to co-owned U.S. Provisional Patent Application Ser. No. 62/625,893 filed Feb. 2, 2018 and entitled "Methods and Apparatus for Human Anatomical Orthoses", the contents of which being incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE DISCLOSURE

Field of the Disclosure

The present disclosure relates generally to orthopedic devices, and in one exemplary aspect to a knee brace with a wraparound sleeve having one or more straps for unloading a knee for treatment of osteoarthritis.

Description of Related Art

Orthopedic devices, such as orthopedic devices that are specifically suited for the knee, have been known to be used for, inter alia, "unloading" the knee that's been affected by osteoarthritis ("OA") in order to, for example, relieve pain. However, prior devices are often considered too bulky, heavy, and/or difficult to put on, thereby making it challenging for patients to want to wear them. Such devices may be configured to impart forces (or leverage) on the limbs surrounding the knee joint in order to relieve compressive forces within a portion of the knee joint, or to otherwise reduce the load on that portion of the knee. The knee is acknowledged as one of the weakest joints in the body and serves as the articulating joint between the thigh and calf muscle groups. The knee is held together primarily by small but powerful ligaments. Knee instability arising out of cartilage damage, ligament strain, and other causes of knee instability is relatively commonplace since the knee joint is subjected to significant loads during the course of almost any physical activity that requires the use of an individuals legs.

Osteoarthritis is a problematic knee pathology, and may arise when there is a persistent uneven distribution of pressure in the medial compartments of the knee. Compartmental osteoarthritis can be caused by, inter alia, injury, obesity, misalignment of the knee, or due to aging of the knee. A major problem resulting from osteoarthritis is that the smooth cartilage lining the inside of the knee wears away. This leads to a narrowing of the joint space due to the development of cysts and erosions in the bone ends. Because of the narrowing of the joint, bone comes directly in contact with bone, and an uneven distribution of pressure develops across the knee, which may cause the formation of bone spurs around the joint. All of these changes ultimately lead to increasing pain and stiffness of the joint.

While there are no cures for osteoarthritis, there are many treatments such as medications, surgery, and non-surgical interventions. Non-surgical interventions include using canes, lateral shoe wedges, and knee braces.

Knee bracing is useful in providing pain relief by reducing the load on the compartment through application of an opposing external valgus moment about the knee joint. Unloading knee braces have been shown to significantly reduce osteoarthritis knee pain while improving knee function. For example, U.S. Pat. No. 5,277,698 filed Aug. 24, 1992 and entitled "Knee Bracing Method", the contents of which being incorporated herein by reference in its entirety, describes a method of reducing the effect of unicompartmental osteoarthritis of a knee. A force is applied to the knee on that side of the knee remote from the compartment having osteoarthritis as the knee moves to extension. Preferably, the force is applied at a point about 10° to 15° posterior of the normal axis of rotation of the knee. U.S. Pat. No. 7,198,610 filed Dec. 21, 2005 and entitled "Knee Brace and Method for Securing the Same", the contents of which being incorporated herein by reference in its entirety describes a knee brace that is divided into anterior and posterior halves including a proximal member and a distal member. The brace further includes a substantially inelastic cross strap adjustable in length and connected to the proximal and distal members. The cross strap has first and second portions which intersect at an intersection point located between the proximal and distal members. The intersection point is defined at a location posterior of the frontal plane of the brace.

Individuals suffering from osteoarthritis of the knee have varying degrees of discomfort and undergo stages of worsening osteoarthritis. Many of the known unloading braces are considered to be too bulky, difficult to put on and very uncomfortable, hence, patients don't want to wear them and they stop being effective. In addition, patients with mild osteoarthritis do not need the most powerful unloading style brace and would therefore be a good candidate for a streamlined brace that is durable while having minimal impact on activities and clothing selections. It may be further desirable that the knee brace has lightweight shells and the brace can be moderately adjusted for differences in patient anatomy and accommodate a wide range of varus/valgus alignments enabling adjustability for unloading force and compressive forces on the leg and knee.

Various soft-good or sleeve braces exist to assist persons with damaged muscle tissue, cartilage and ligaments in the knee area, but few treat osteoarthritis of the knee. The sleeve braces often rely on elasticity of the sleeve to snugly hold the knee by enclosing the knee in either a tubular configuration or a wrap-type brace that is openable and wraps about the knee to form a tubular configuration. Others may still rely on a hinge to push the knee, however when attached into a soft brace, the hinge tends to move away from the leg.

An advantage of the soft braces is that the tubular configuration may apply radial compression to the knee, and straps may increase the radial compression on the knee. Disadvantages occur in that the stretch ability of the soft braces may be too tight, and either be too restrictive or insufficiently restrictive to movement. Various strapping arrangements have been proposed that attempt to cure the deficiencies but many lack effectiveness to truly unload the knee and relief pain from osteoarthritis. Few knee braces have been able to harmonize effective unloading of the knee in combination with a sleeve-type brace without the necessity of a substantial frame system. It has been difficult to present a solution that mitigates rotation and migration of the sleeve from unloading of the knee, while providing therapeutic compression. For example, the more powerful Unloader-type braces known in the art include a double strap that tends to cause discomfort in the popliteal region due to the crossing of the straps in the back of the knee. The more conventional Unloader style braces with a single strap cause the brace to rotate on the leg, making it difficult to correctly place on the user's anatomy.

Accordingly, despite the wide variety of the foregoing solutions, there remains a salient need for an orthopedic device that: provides adequate support for everyday use; is comfortable to wear; is inexpensive; is easy to put on and take off; is adjustable so as to accommodate various unique anatomies; doesn't rotate on the leg like conventional single strap designs do and doesn't cause the excessive pressure in the popliteal like the double strap braces do and fits well with existing clothing.

SUMMARY

The present disclosure satisfies the foregoing needs by providing, inter alia, an orthopedic device for addressing one or more of the foregoing desirable traits as well as methods of their manufacture and methods of their use.

In one aspect, an orthopedic device is disclosed. In one embodiment, the orthopedic device includes a first panel defining opposed first and second sides; a second panel having a first end secured to the first side of the first panel along a seam, and a second end securable to the second side of the first panel at a location site; and a first strap having a first end secured to the first side of the first panel along the seam and laying under the second panel, and a second end securable to the second side of the first panel at the location site.

In one variant, the orthopedic device includes a dynamic force strap that helically extends between upper and lower portions of the orthopedic device and connecting to the first panel.

In another variant, a hinge assembly is secured to the first panel and extends between upper and lower portions of the orthopedic device.

In yet another variant, the orthopedic device includes a second strap having a first end secured to the first side of the first panel along the seam and laying under the second panel, and a second end securable to the second side of the first panel at the location site.

In yet another variant, a second dynamic force strap helically extends from around the center of the first dynamic force strap and connecting to the first panel opposite where the first dynamic force strap connects.

In yet another variant, both the first dynamic force strap and the second dynamic force strap are adjustable in length.

In another embodiment, an orthopedic device is disclosed that includes a hinge assembly secured and slidable in relation to a thigh shell and a calf shell. The slidable relation works in conjunction with a push button.

In a variant, the orthopedic device includes keyholes for attachment of D rings and straps; ventilated shells for breathability, soft good attached to the thigh shell consists of a first panel defining opposed first and second sides; a second panel having a first end secured to the first side of the first panel along a seam between upper and lower corners of the seam, and a second end defining at least one flap securable to the second side of the first panel at a location site; a first strap having a first end secured to the first side of the first panel and extending from an upper portion of the seam including the upper corner of the seam and overlying at least a portion of the second panel, and a second end securable to the second side of the first panel at the location site; soft good attached to calf shell consists of a first panel defining opposed first and second sides; a second panel having a first end secured to the first side of the first panel along a seam between upper and lower corners of the seam, and a second end defining at least one flap securable to the second side of the first panel at a location site; a first strap having a first end secured to the first side of the first panel and extending from an upper portion of the seam including the upper corner of the seam and over-lying at least a portion of the second panel, and a second end securable to the second side of the first panel at the location site; a dynamic force strap helically extending between upper and lower portions of the orthopedic device and connecting to the first panel; a hinge assembly secured to the first panel and extending between upper and lower portions of the orthopedic device, the dynamic force strap has first and second ends securing to first and second frames of the hinge assembly spaced apart by first and second struts connected to one another by a hinge; and a second dynamic force strap helically extending from around the center of the first dynamic force strap and connecting to the first panel opposite where the first dynamic force strap connects.

In one variant, a third dynamic force strap helically extends from around the center of the first dynamic force strap and connects to the first panel on calf support opposite where the first dynamic force strap connects on that same calf support.

In another variant, the second dynamic force strap connects at the center of the first dynamic force strap through means such as a key hole locking system allowing it to pivot.

In yet another variant, the first panel is adjustable in length through trimming to allow for proper sizing.

In another embodiment, the orthopedic device, includes: a first panel having a thigh attachment feature and a calf attachment feature, the first panel having a first seam edge and a second opposing edge, the second opposing edge including a first flap for the thigh attachment feature and a second flap for the calf attachment feature; a second panel that is attached to the first panel at the first seam edge, the second panel having a first portion and a second portion, the first portion being separated by the second portion by a gap, the gap comprising a separation feature; a first strap that extends from a first strap seam located on the second panel towards the second opposing edge of the first panel; and a second strap that extends from a second strap seam located on the second panel towards the second opposing edge of the first panel.

In one variant, the first strap seam is spaced from the first seam edge by a first distance and the second strap seam is spaced from the first seam edge by a second distance.

In another variant, the first distance is the same as the second distance.

In yet another variant, the first portion of the second panel includes a first plurality of trim lines and the second portion of the second panel includes a second plurality of trim lines.

In yet another variant, the first plurality of trim lines and the second plurality of trim lines are configured so as to accommodate a plurality of different lower extremity circumferences for a user of the orthopedic device.

In yet another variant, the first strap includes a third flap that is disposed generally adjacent to the second opposing edge of the first panel and the second strap includes a fourth flap that is disposed generally adjacent to the second opposing edge of the first panel.

In yet another variant, the first flap, the second flap, the third flap and the fourth flap are each configured to be attached to one of the first portion of the second panel or the second portion of the second panel.

In yet another variant, the second panel further includes a first pocket and a second pocket, the first pocket and the second pocket being configured to receive a hinge assembly therein.

In yet another variant, the hinge assembly includes: a thigh plate that includes a first attachment ring and a second attachment ring; a calf plate that includes a third attachment ring; and a hinge mechanism that is coupled to the thigh plate and the calf plate.

In yet another variant, the first pocket includes a first slot that is configured to receive the first attachment ring and a second slot that is configured to receive the second attachment ring; and the second pocket includes a third slot that is configured to receive the third attachment ring.

In yet another variant, the orthopedic device further includes a dynamic force strap having a first end, a second end, and a third end, the first end configured to be attached to the first attachment ring, the second end configured to be attached to the second attachment ring, and the third end configured to be attached to the third attachment ring, the dynamic force strap, when coupled to the first, second and third attachment rings is configured to unload a knee of a wearer of the orthopedic device.

In another aspect, methods of utilizing the aforementioned orthopedic device are disclosed. In one embodiment, a method for securing an orthopedic device to a leg and about a knee may involve using the orthopedic device by placing the orthopedic device in a flat configuration posterior of the knee and leg; locating the seam along a posterior or a second side of the knee and leg; wrapping the second strap from the seam about a first side of the leg and knee; wrapping the first strap from the seam about a second side of the leg and knee; wrapping the second panel around the leg from the seam and securing first the bottom flap followed by the top flap. Lastly the dynamic force strap is engaged through a D ring attached at the thigh shell after having first and only during initial application of the brace, having adjusted and attached the second strap which engages in the thigh frame at the opposite side of the D ring.

In yet another aspect, a frame assembly for use with the aforementioned orthopedic device is disclosed.

Other features and advantages of the present disclosure will immediately be recognized by persons of ordinary skill in the art with reference to the attached drawings and detailed description of exemplary implementations as given below.

Figure 1A:
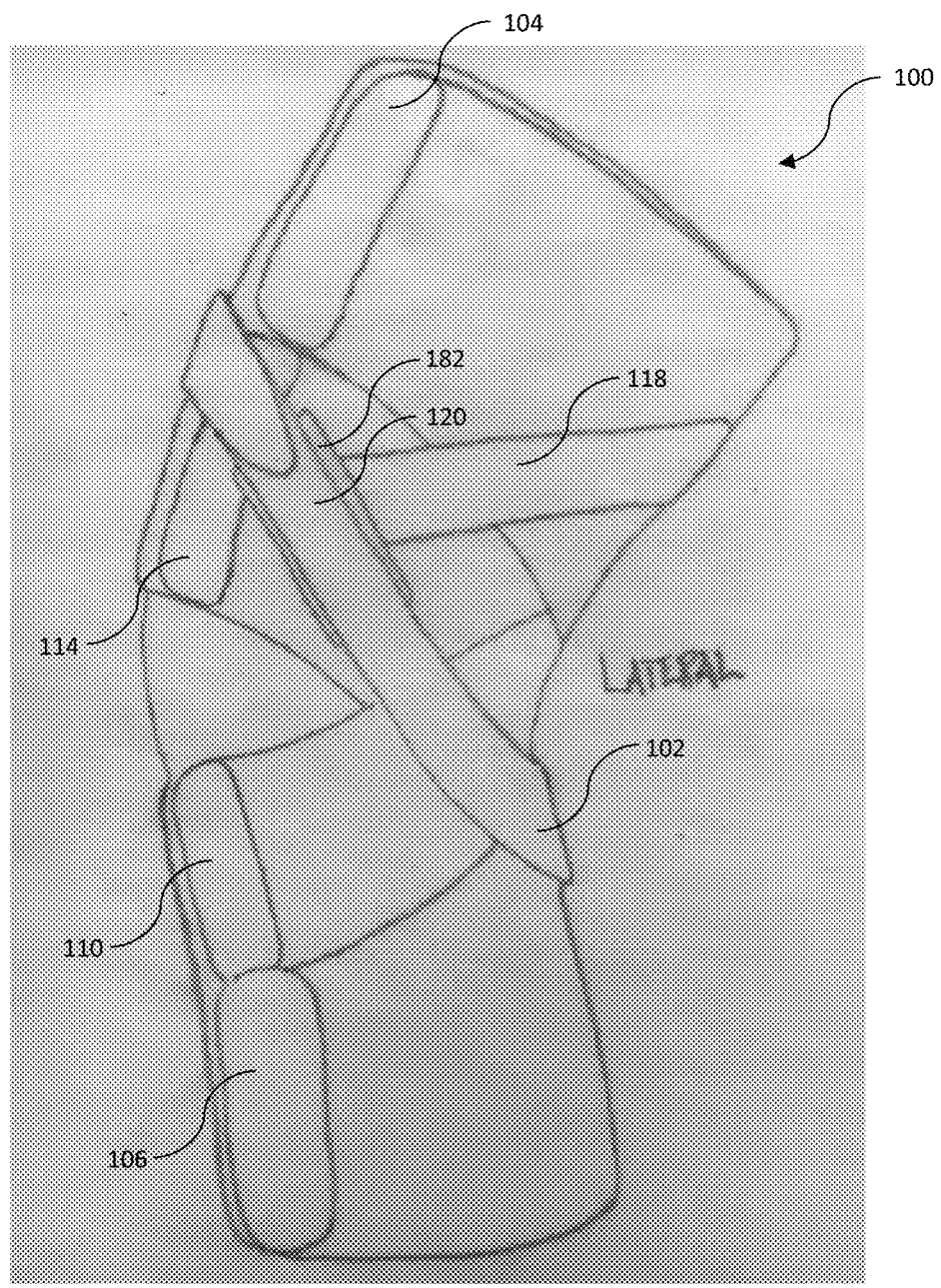
FIG. 1A is a view of an exemplary orthopedic device with a Y Unloading strap shown on the lateral side of the device, in accordance with the principles of the present disclosure.

All Figures disclosed herein are © Copyright 2018-2019 Arni Thor. All rights reserved.

DETAILED DESCRIPTION

Implementations of the present technology will now be described in detail with reference to the drawings, which are provided as illustrative examples so as to enable those skilled in the art to practice the technology. Notably, the figures and examples below are not meant to limit the scope of the present disclosure to any single implementation or implementations, but other implementations are possible by way of interchange of, substitution of, or combination with some or all of the described or illustrated elements. Wherever convenient, the same reference numbers will be used throughout the drawings to refer to same or like parts.

Moreover, while embodiments described herein are primarily discussed in the context of an orthopedic device having a hinge positioned on the medial side of the device with the straps positioned on the lateral side of the knee brace, it would be readily apparent to one of ordinary skill that the orthopedic devices described herein are not so limited. Alternative arrangements would be readily understood by one of ordinary skill given the contents of the present disclosure that the orthopedic device may be configured to reduce or cure both medial and/or lateral knee joint infirmities. For example, the hinge may be positioned on the lateral side of the knee brace and the straps may be positioned on the medial side of the knee brace in some implementations. These and other arrangements would be readily understood given the contents of the present disclosure.

Referring now to FIGS. 1A-1I various unloading style braces (orthopedic devices 100) that may include a wrap-around sleeve, a single upright frame (170, 154, 168, 156, 162, 164) and a Y strap unloading feature 102, 118 are shown and described in detail. Implementations of the orthopedic device 100 described herein provide for a knee brace of an unloading type which harmonizes the use of a dynamic force strap 102 with a sleeve-type brace in order to unload a knee that may have, for example, osteoarthritis while simultaneously resisting rotation caused by the tightening of the dynamic force strap 102. As a brief aside, prior orthopedic devices (such as that described in U.S. Pat. No. 5,277,698, the contents of which were previously incorporated herein by reference in its entirety) tend to cause the orthopedic device to rotate about the leg when the strap on these devices was tightened. Contrast with the Y strap unloading feature 102, 118 depicted which may be constructed from an elastic (or semi-elastic) material in some implementations unlike prior devices which utilize an inelastic strap. The Y strap unloading feature 102, 118 provides for a distinct advantage over prior orthopedic devices. Additionally, the second strap 118 advantageously avoids the popliteal region of a wearer's anatomy (i.e., the hollow at the back of the knee) in some implementations. This makes the orthopedic device 100 more comfortable to wear as the placement of the second strap 118 avoids irritating this region of a wearer's anatomy.

Additionally, the orthopedic devices 100 described herein may provide sufficient compression about the leg and knee while containing various features that enable adjustability so as to accommodate a wide variety of unique anatomies. In some implementations, the orthopedic device 100 is placed around the leg and knee via the wrapping of the orthopedic device 100 around the leg and knee. This has advantages over prior devices as these prior device were often of a fixed tubular shape and hence necessitated that the device be pulled up over the foot and placed over the leg and knee. However, it would be readily apparent to one of ordinary skill the orthopedic device 100 may be adapted to have a fixed tubular shape in some implementations. A single dynamic force strap may be effective to unload the knee in a soft dynamic way, however it may also tend to cause the brace to rotate around the leg. Implementations of the present disclosure utilize the Y strap configuration which uses a dynamic force strap 102 and a second strap 118 that connects to the dynamic force strap above the popliteal, opposite of the hinge, spirals around the leg to the thigh shell 164 on the opposite site of where the dynamic force strap connects to the thigh shell and therefore resists the rotation forces without creating bulk or discomfort in the popliteal region as is present in prior devices. Additionally, such a Y strap unloading feature may reduce the complexity of donning and doffing as compared with prior devices.

In some implementations, the orthopedic device 100 may be provided for low to moderate active users with mild-to-moderate symptoms of unicompartmental osteoarthritis, although it is not limited to such uses. The closure system which consists of the two flaps 104, 106 on the second panel 108 as well as the individual flaps 110 on the first strap 112 and individual flap 114 on the second strap 116 of the wrap around configured orthopedic device 100 may be provided to assist patients with poor hand strength or dexterity while still providing improved compression and suspension of the orthopedic device 100 as compared with prior devices. The orthopedic device 100 has a wrap-around design arranged for easily wrapping about a wearer's leg, and enables a simple donning procedure. Unloading of the wearer's knee by the orthopedic device is achieved by a dynamic force strap 102 which is simple to adjust and may provide a gentle force applied to the knee. Rotation and additional unloading is then controlled by a second force strap 118 that connects from around the center 120 of the dynamic force strap 102, opposite of the frame assembly 122 and transfers up the leg to connect to the thigh frame 124, opposite from the connection of the dynamic force strap. This second force strap 118 therefore creates an opposite force at the thigh to combat the rotation which occurs when the dynamic force strap 102 is tightened.

In some implementations, the orthopedic device 100 may include a first panel 126 composed of opposed first 128 and second sides 130, a second panel 132 having a first end 134 secured to the first side of the first panel along a seam 136, and a second end 138 securable to the second side of the first panel at a location site 140. The first panel 126 and the second panel 132 may be constructed from similar materials as the aforementioned straps 102, 118. A first strap 112 has a first end 142 secured to the first side of the first panel along the seam and lies underneath the second panel 132, and a second end 144 securable to the second side of the first panel at the location site 146 at the thigh. A second strap 116 has a first end 148 secured to the first side of the first panel 126 along the seam 136 and lies underneath the second panel 132, and a second end 150 securable to the second side of the first panel at the location site 152 which is disposed at the calf when worn by a user. A dynamic force strap 102 helically extends between upper and lower portions of the orthopedic device 100 and connects to the first panel 126. The second force strap 118 connects to the center 120 of the dynamic force strap 102 at a location opposite of the hinge assembly 154, travels up the leg, opposite of the dynamic force strap 102 and connects to the thigh frame 156, opposite of the dynamic force strap connection. The hinge assembly 154 secures to the first panel 126 and extends between upper and lower portions of the orthopedic device. The dynamic force strap 102 has first 158 and second ends 160 securing to first 162 and second frames 164 of the hinge assembly that are spaced apart by first 166 and second struts 168 connected to one another by a hinge 170.

An orthopedic device 100 may include a hinge 154 attached to a thigh shell 164 and a calf shell 162 (see also FIGS. 2A-2E). Such a frame may be attached to a sleeve that includes a first panel 126 defining opposed first 128 and second sides 130. A second panel 108 has a first end 148 secured to the first side of the first panel along a seam 128 between the upper 178 and lower corners 180 of the seam, and a second end 138 defining at least one flap 104 securable to the second side of the first panel at a location site 146. A first strap 112 has a first end 142 secured to the first side of the first panel below the second panel. A second strap 116 has a first end 148 secured to the first side of the first panel below the second panel and overlays at least a portion of the first strap. A dynamic Y force strap helically extends between the upper and lower portions of the orthopedic device and connects to the first panel. Such a strap splits into a second strap around knee center, above the popliteal, opposite of the hinge, which spirals in the opposite direction of the first end to attach on the opposite side of the first panel. Such an orthopedic device may contain a height adjustment mechanism so that the frame could be lengthened or shortened without tools in order to accommodate different leg lengths.

Figure 1B:
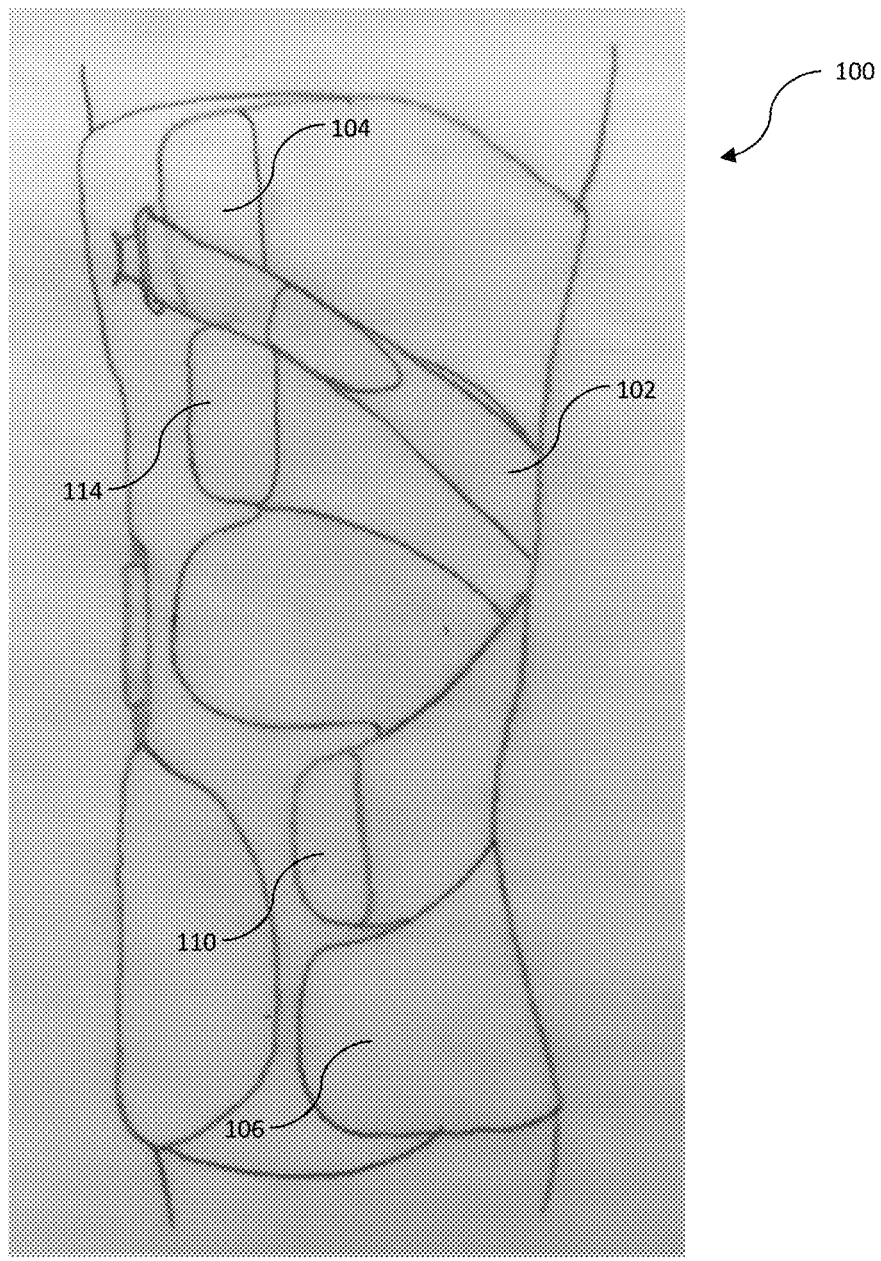
FIG. 1B is a front view of the orthopedic device of FIG. 1A shown on the front side of the device, in accordance with the principles of the present disclosure.
Figure 1C:
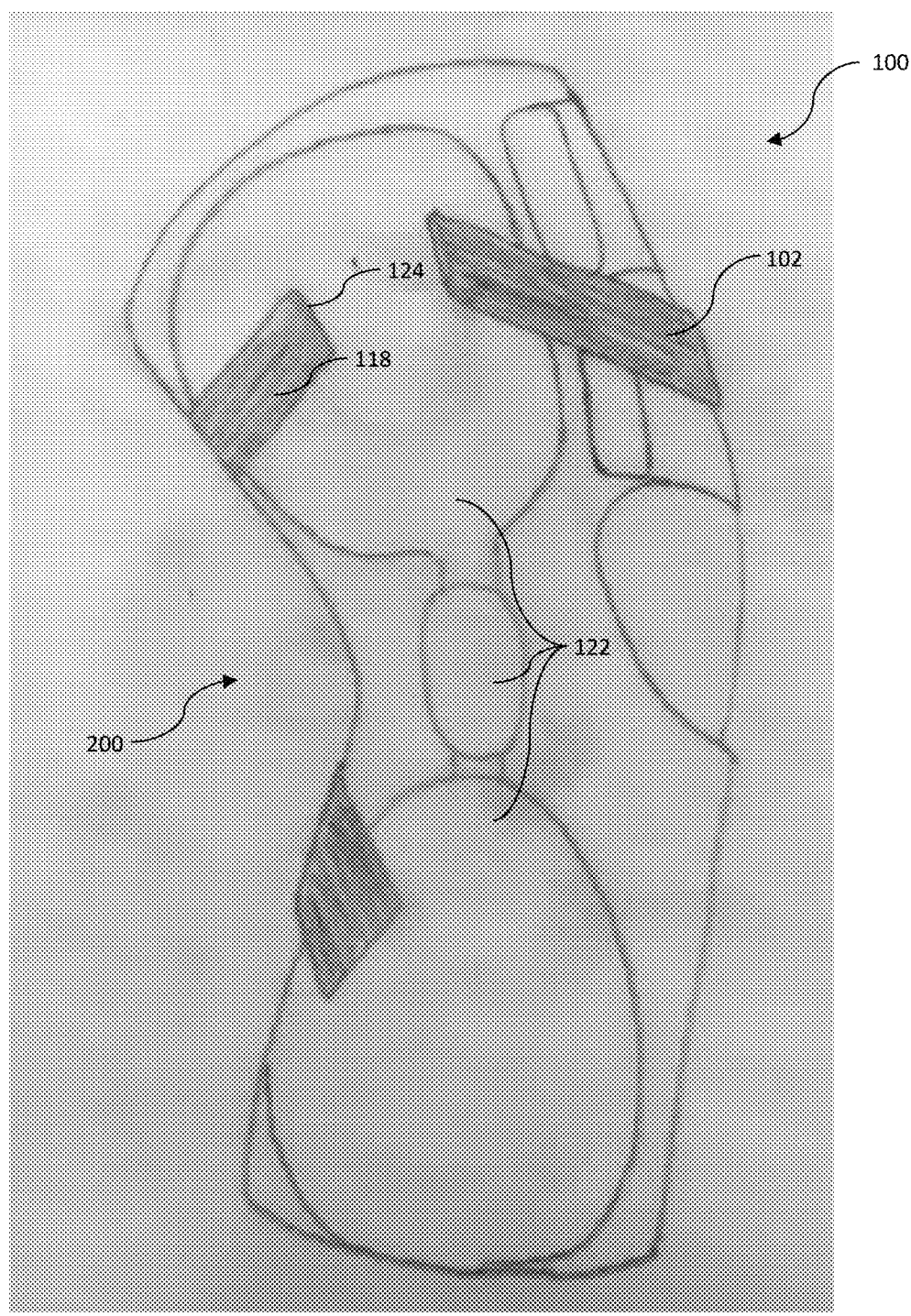
FIG. 1C is a view of the orthopedic device of FIG. 1A shown on the medial side of the device, in accordance with the principles of the present disclosure.

FIGS. 1A-1C show the Y strap configuration using a connection mechanism such as, for example, Velcro. The so called half strap 118 that creates the Y can be attached to the dynamic force strap 102 using Velcro or any other means of removable (or fixed) attachment that would be readily understood by one of ordinary skill given the contents of the present disclosure. In some implementations, the straps 102, 118 are made from a class of materials that are soft to the touch and have good elasticity and bounce back in order to provide, inter alia, sufficient compression around the leg. Such elasticity provides additional comfort for the wearer of the orthopedic device as compared with prior devices that utilize a non-elastic strap. In some implementations, the materials chosen for the straps 102, 118 enable good breathability. As a brief aside, breathability is the ability of a fabric to allow moisture vapor to be transmitted through the material. Note that while air permeable fabrics tend to have relatively high moisture vapor transmission, a breathable material doesn't necessarily require that the fabric be air permeable in some implementations. Exemplary materials include, for example, neoprene (preferably neoprene that has been ventilated for increased breathability), an Aerospacer base mesh fabric (which may be constructed from Nylon and spandex fibers), a laminate material constructed from nylon, spandex, polyester and/or lycra, or other materials that provide, for example, good elasticity and bounce back as well as breathability.

A semi rigid (or rigid) plate 164 may be attached to the dynamic unloading strap 102 via a variety of means. For example, in some implementations this attachment may be accomplished with a keyhole (see e.g., keyhole 210 on FIG. 2E). One end of the short strap 118 may also include a variety of means for attachment. For example, in some implementations this attachment may be realized via a button hook that is secured (e.g., sewn) so that it may "snap" onto the thigh plate 182 that is attached firmly to the dynamic unloading strap 102. This allows the short strap 118 to pivot and align with the thigh to wrap around and attach to the thigh plate 164. Both strap ends attach to the thigh plate 164 as can be seen on FIG. 1C. Both straps may be adjusted using, for example, Velcro, Velcro through a D ring, BOA cable mechanism, ratchet, combinations of the foregoing or any other form of tightening/attaching mechanism.

Figure 1D:
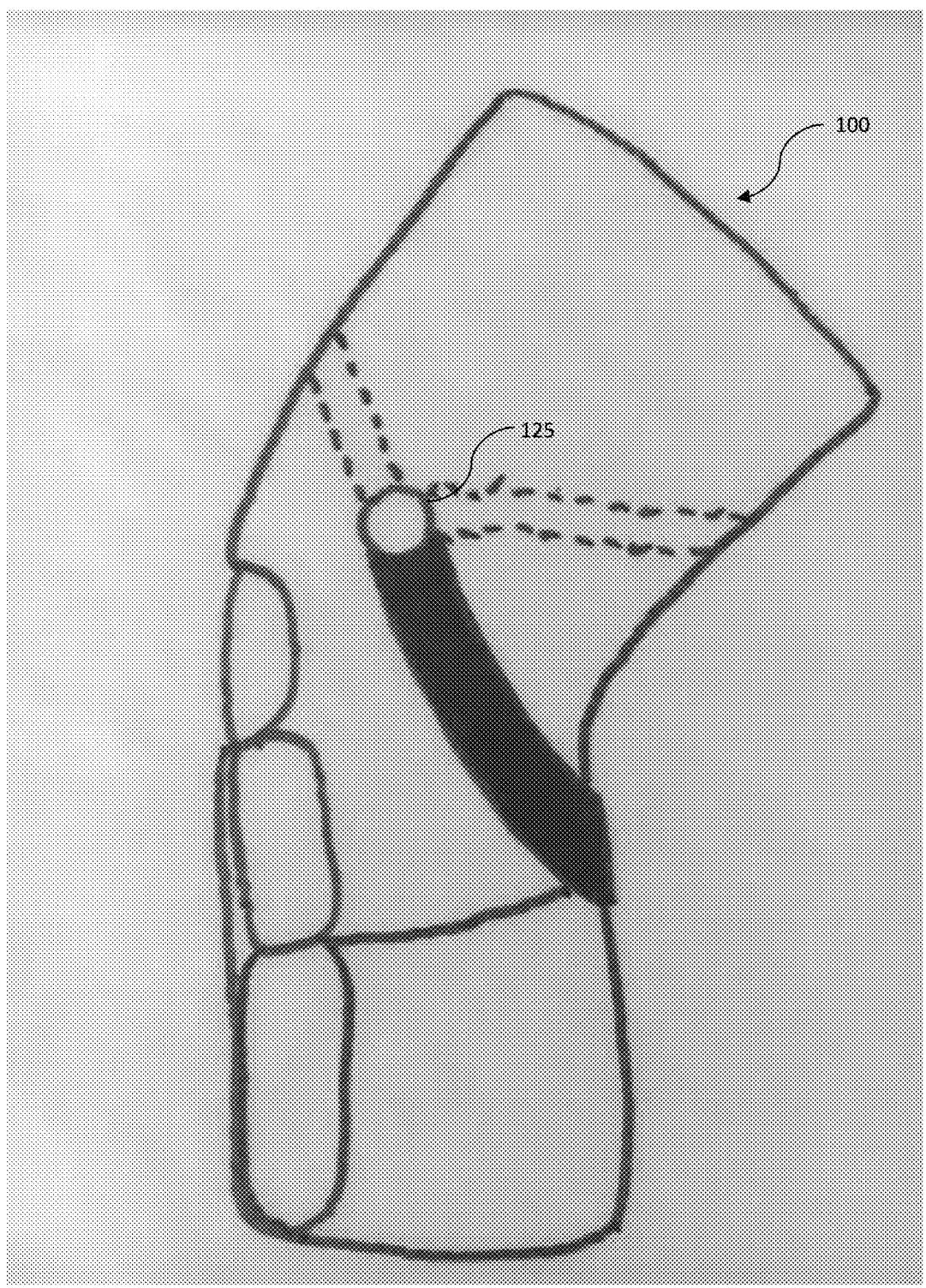
FIG. 1D is a view of yet another exemplary orthopedic device with the Y Unloading strap from FIG. 1A using a rotary tensioning mechanism, in accordance with the principles of the present disclosure.
Figure 1E:
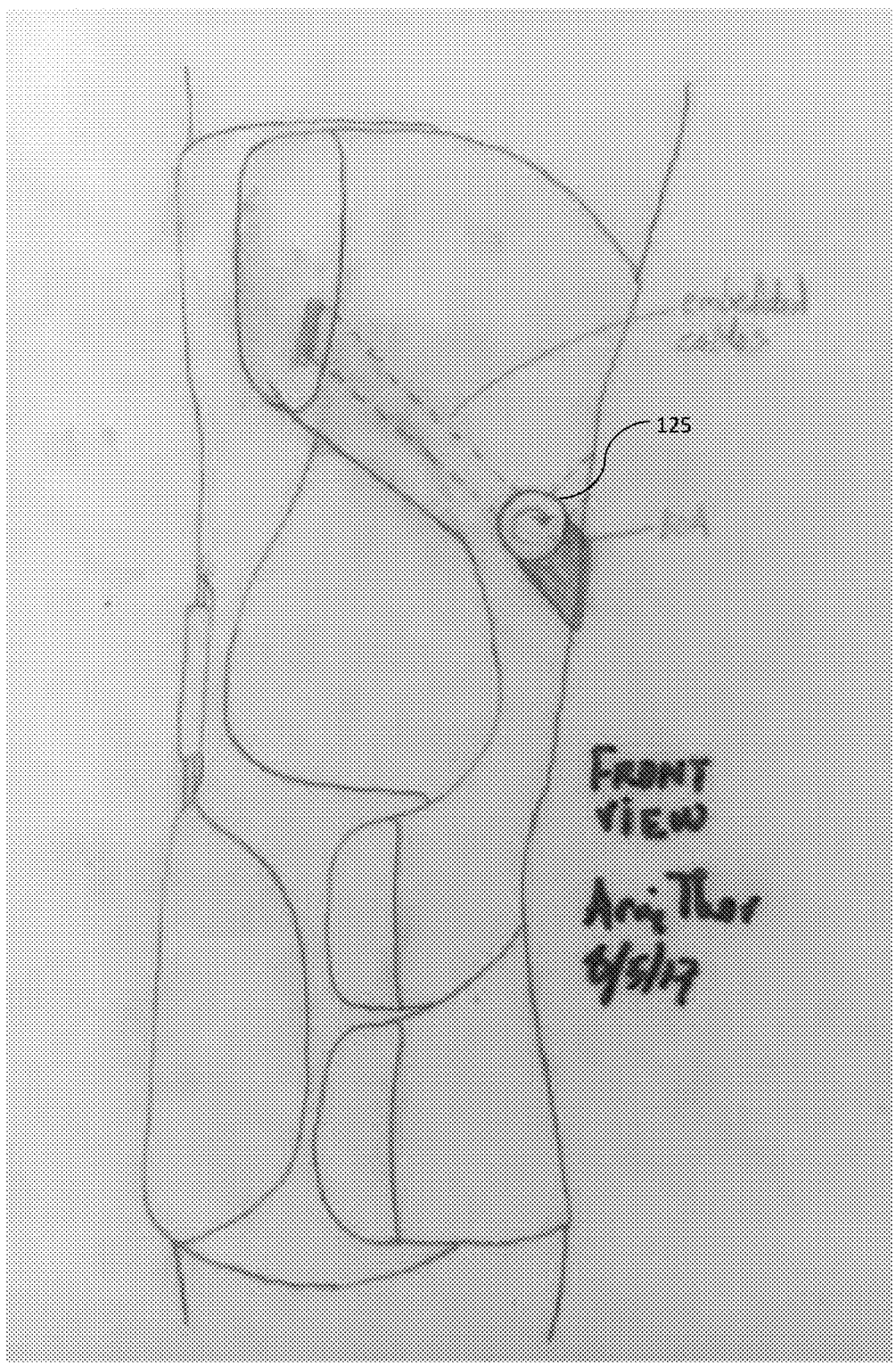
FIG. 1E is a front view of the orthopedic device of FIG. 1D on the front side of the device, in accordance with the principles of the present disclosure.

FIGS. 1D and 1E show how the Y strap can be controlled with a single tensioning mechanism 125 (e.g., a BOA mechanism). In this illustrated configuration, a single BOA dial or any other form of a tightening mechanism may be placed at the location where the strap separates into two straps. Cables may be embedded into the fabric of the sleeve or be visible and attached with guides on the outside of the sleeve. The offloading component may therefore, be controlled through tightening of, for example, a single dial and all strap ends may be fixed to the frame (e.g., two at the thigh shell and one on the calf shell). There may additionally, include an initial adjustment feature on both strap ends located on the thigh shell to ensure that the straps are adjusted enough to provide proper and even unloading when the tightening occurs.

Figure 1F:
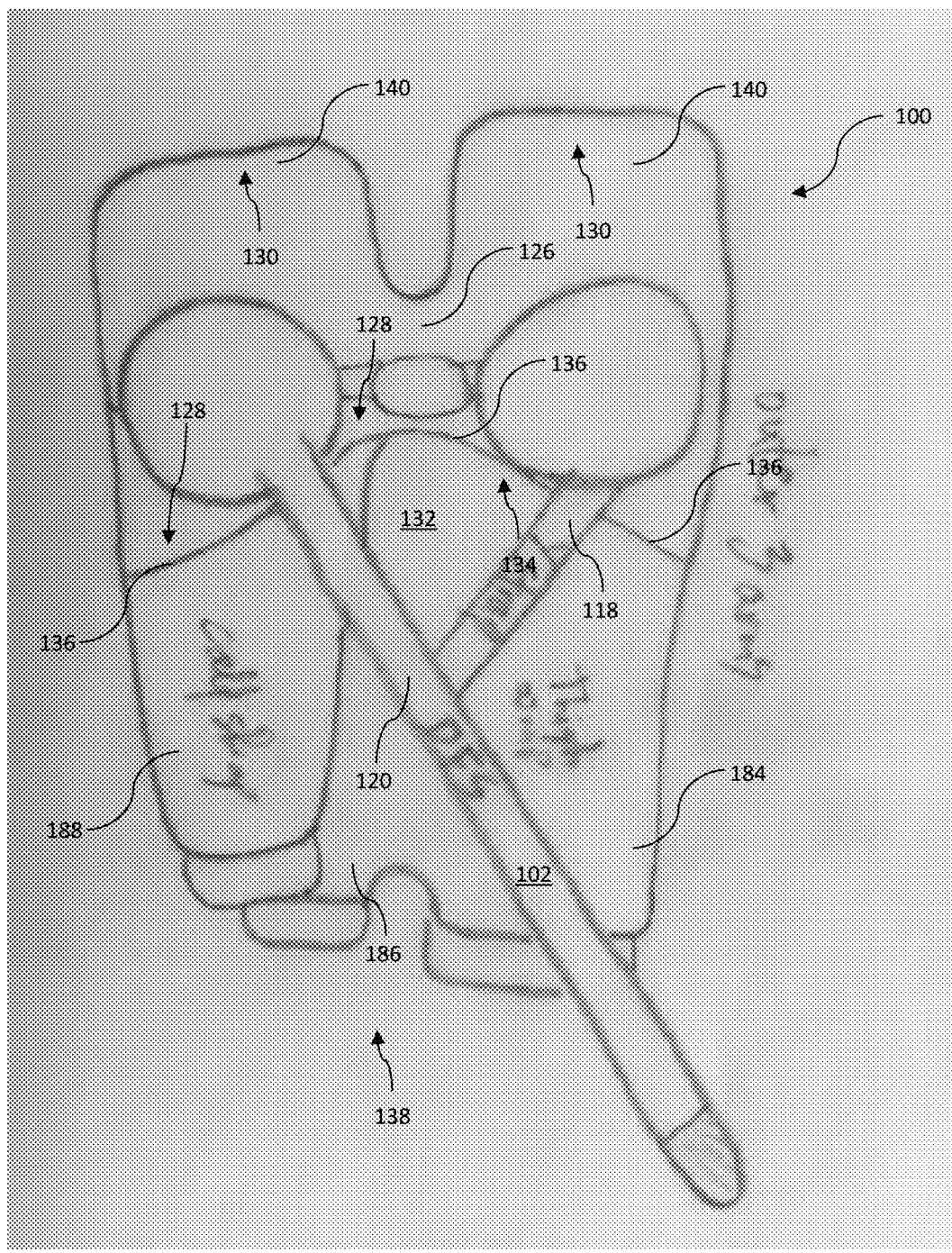
FIG. 1F is a flat view of a sleeve used in the Y Unloading strap orthoses, in accordance with the principles of the present disclosure.
Figure 1G:
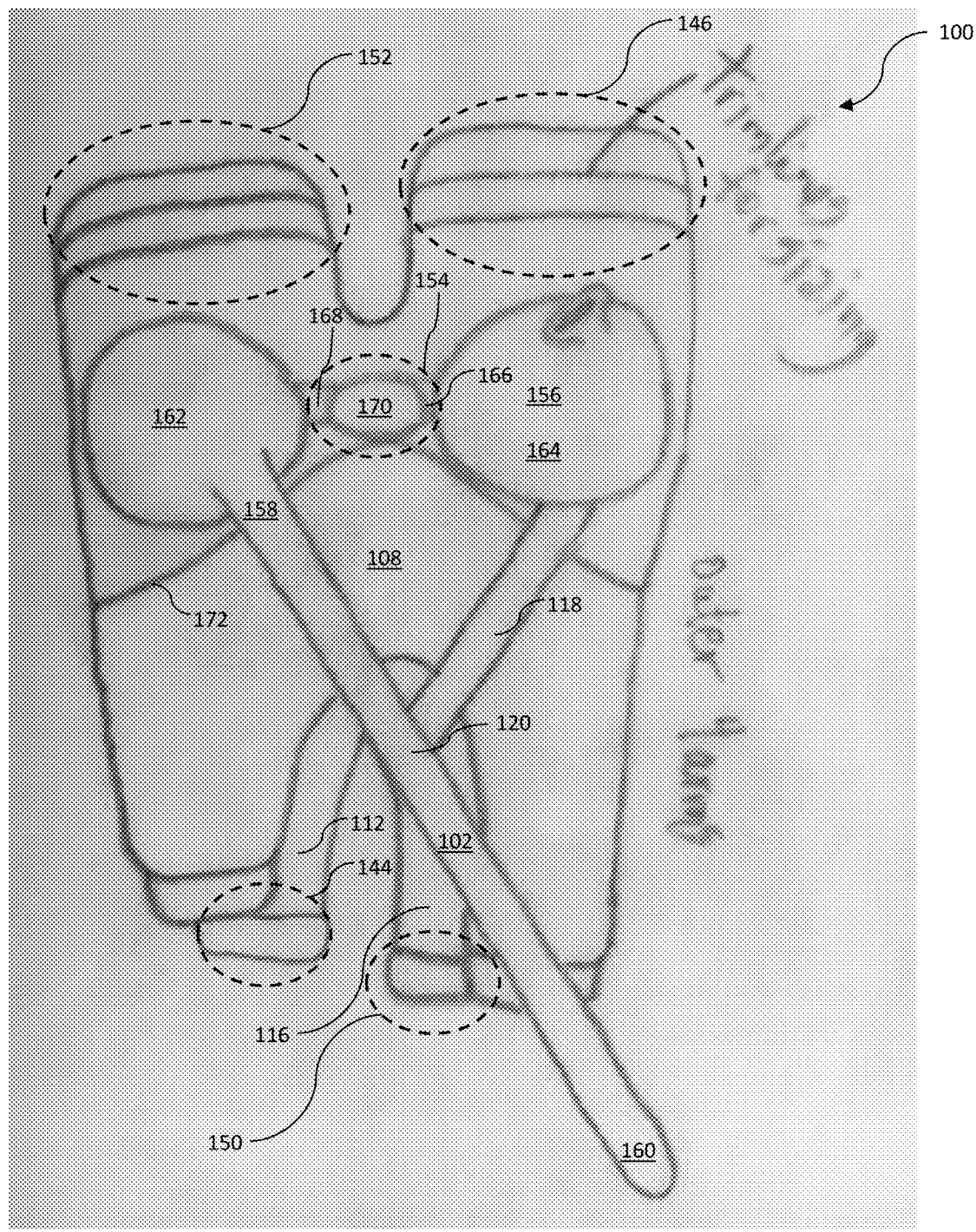
FIG. 1G is a flat view perspective of another sleeve configuration used in the Y Unloading strap orthoses (showing the gastric and the lower thigh underneath the panel), in accordance with the principles of the present disclosure.
Figure 1H:
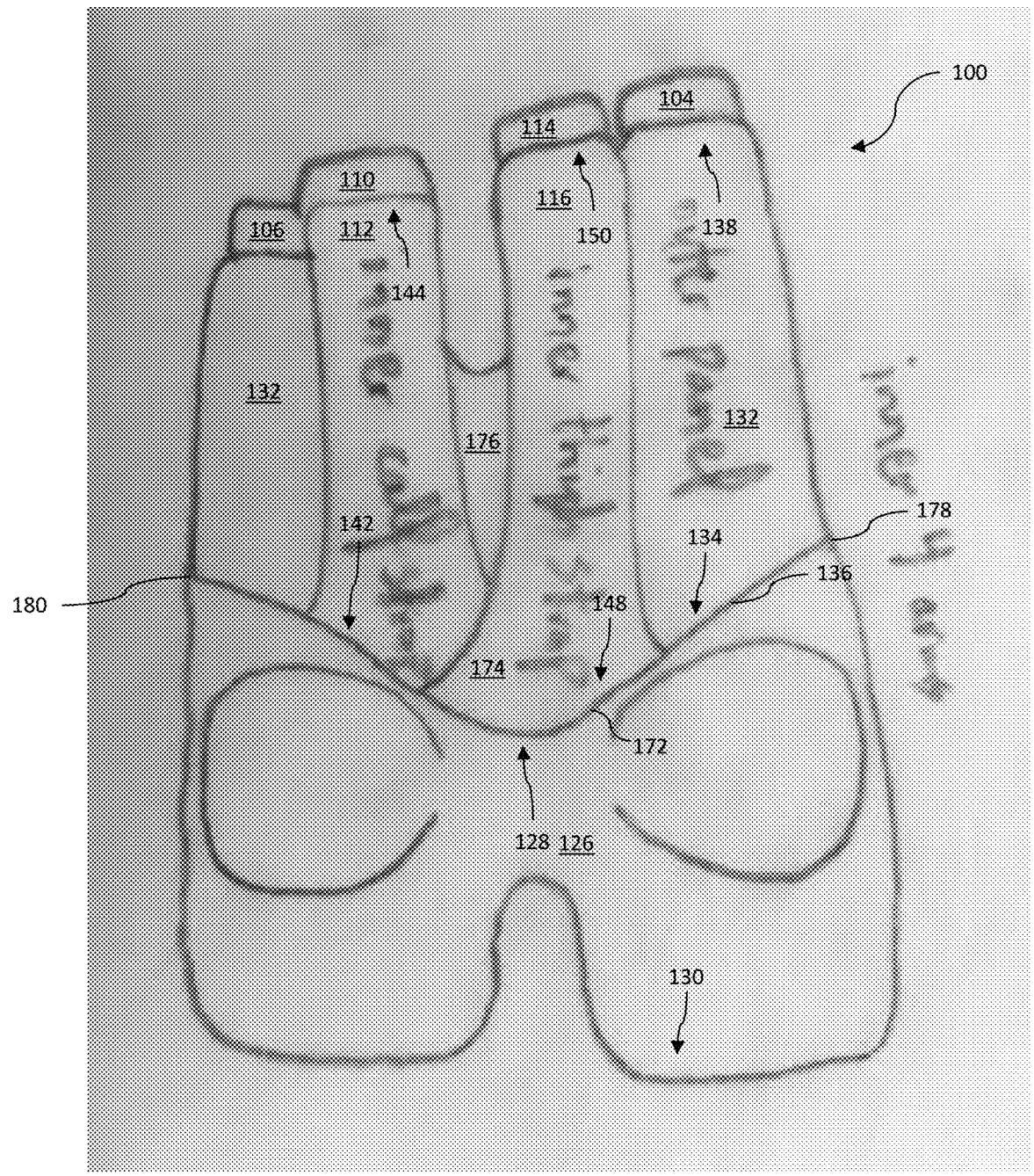
FIG. 1H is a flat view perspective of the configuration of FIG. 1G shown from the opposite side, in accordance with the principles of the present disclosure.

FIGS. 1F-1H illustrate how the sleeve may be constructed using a wraparound sleeve configuration that includes three to four attachments respectively. FIG. 1F shows a three-flap configuration with a single wide flap at the thigh and two tabs on the calf. Such a configuration may aid the user with donning of the device, especially on the calf by providing, for example, a secure elastic suspension strap 112 that is easy for the user to pull on. The number of steps required to don the brace may be fewer as compared to, for example, a four-flap design.

FIG. 1F shows a flat view of the three-flap configuration with one wide thigh flap 184 that connects to the upper calf flap 186 and then a separate lower calf strap 188 which can either sit underneath or above the thigh/calf panel flaps. This lower calf strap could also be positioned as the upper calf strap (not shown) to provide very secure suspension and sit underneath the thigh/calf flap. In that configuration the thigh/calf flap would consist of the thigh flap and the lower calf flap. According to an embodiment, in an open, flat configuration, the first flap is located at least in part above the second end of the first strap, and the second flap is located at least in part below the second end of the second strap relative to the upper corner of the seam. In a closed, wrapped configuration, the first flap is still located above the second end of the first strap and borders the patella opening of the orthopedic device 100. Tensioning of the first and second straps is arranged independently of tensioning of the second panel via the first and second flaps. The first strap is arranged to be secured to the second side of the first panel independently from the second strap such that the first and second straps are separated by a clearance at the seam. The straps engage the first panel prior to the second panel flaps in a closed wrap configuration. The second strap acts as a suspension strap right above and around the belly of the calf and is attached first. Second is the first strap that comes above the knee on the lower thigh section. Finally the second panel flaps are engaged, first the lower one at the bottom of the calf and then the upper flap at the top of the thigh.

In the configuration illustrated in FIG. 1G (an outer flat view), the user starts by applying two straps, one above the calf and one on the lower thigh. The patient applies a wide panel that includes the bottom calf attachment 106 and the top thigh attachment 104. The two straps sit underneath the wide outer panel 108. Prior to donning the brace, the user (or fitter) may use predetermined trim lines 146 shown in order to adjust the brace to the appropriate circumference size for both thigh and calf. Another possible circumference adjustment is through a wide alligator clip that can be added onto flap to lengthen brace circumference. The user (or fitter) may also alter the height of the brace by pushing buttons on thigh shell and calf shell that engage with arms on the hinge to lengthen or shorten the frame by pulling the shells away from the hinge center or pushing the shells towards the hinge center. The sleeve has sufficient vertical elasticity to accommodate the different frame lengths.

FIG. 1H shows the inner flat view of the orthopedic device shown in FIG. 1G. The first strap 112 preferably extends from the seam 136 and relative to the first panel 126. The seam 136 defines a profile with at least one curved segment 172, and the first strap 112 is located along the curved segment. A second strap 116 preferably extends above the lower portion of the seam and the first strap 112 extends below the upper portion of the seam. A lower edge 174 of the second strap 116 may overlap the upper edge of the first strap 112. A clearance may be defined between the first and second straps at certain locations 176 and the clearance is greatest in height furthest away from the seam. The second strap 116 may have a longer length than a length of the first strap 112. The second panel preferably defines at least one flap 104 located at the second end. The at least one flap may include fastener material for engaging corresponding fastener material located at a second side of the first panel. For example, the at least one flap may comprise first 104 and second flaps 106 spaced apart by a gap so that a patella opening is formed in combination with the second side of the first panel. An exemplary usage scenario for some implementations of the flaps (straps) 104, 114, 110, 106 depicted in FIG. 1H is now described. The combination of straps 112, 116 and panel 132 serves to contain the soft tissue around the knee of the wearer and to hold the orthopedic device 100 on the leg of the wearer. Flap 104 may connect to the top portion of the second panel 132 and therefore constitutes the top strap (i.e., the strap positioned on the thigh of the wearer). Flap 114 may connect to the second strap 116 from the top. Flap 110 may connect to the first strap 112 which is the second from the bottom and flap 106 may connect to the bottom portion of the second panel 132 and therefore constitutes the bottom strap. Straps 112 and 116 are separate straps and flaps 104 and 106 may be connected to the same panel which come over straps 112 and 116. One exemplary benefit of this disclosed configuration is that for suspension. Namely, strap 112 may be the most important of the straps for suspension and is the first one that is applied first in order to make sure that the brace stays on the leg well.

Figure 1I:
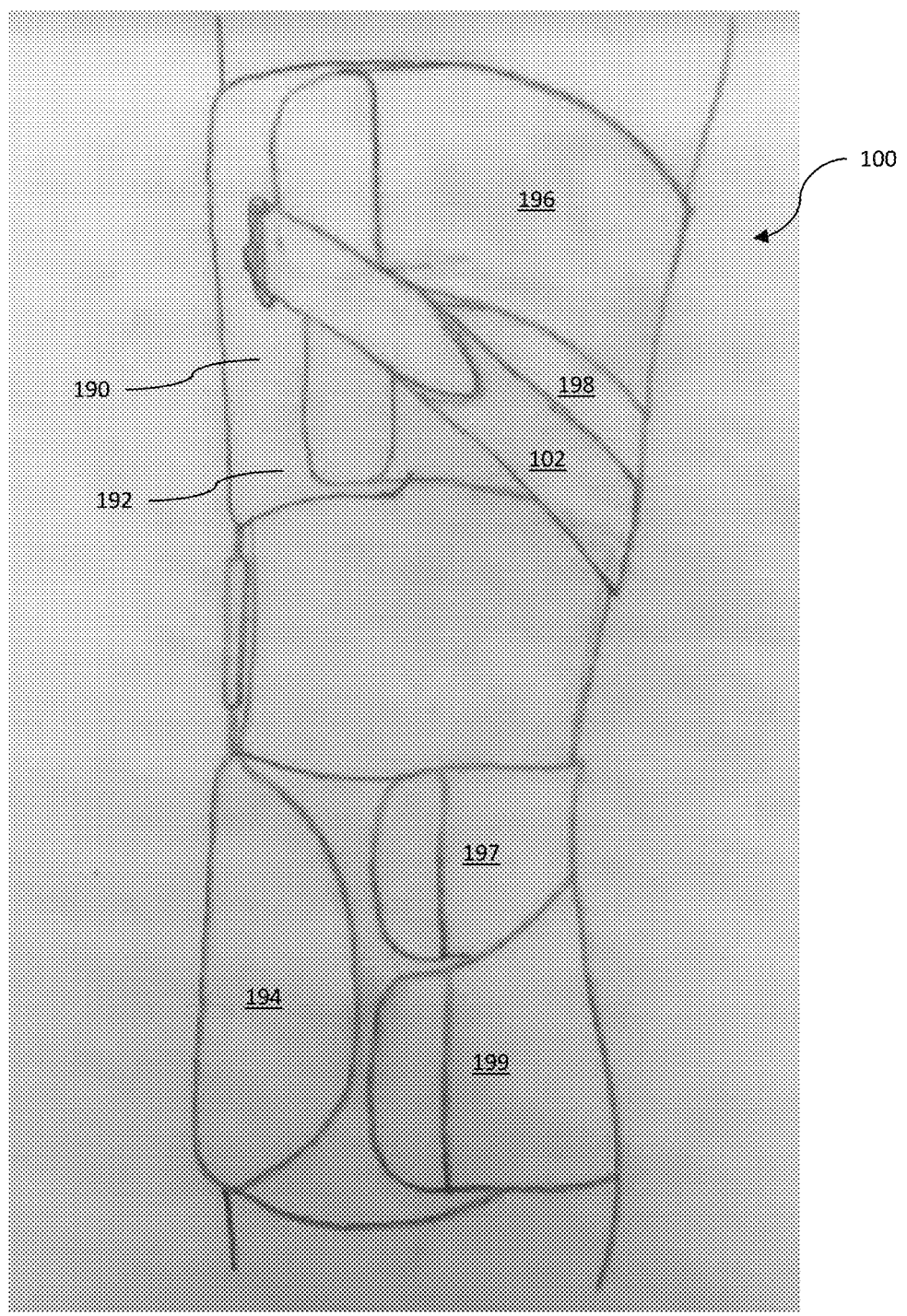
FIG. 1I is a front perspective view of the configuration shown in FIG. 1G and/or FIG. 1H in which the sleeve has been separated, in accordance with the principles of the present disclosure.

FIG. 1I shows two wraps, where one wrap 190 is applied to a thigh shell 192 and the other wrap is applied to a calf shell 194. Both wraps include two straps 196, 198, 197, 199 respectively to make sure that the donning is easy and effective in tension for the user. This provides a very secure suspension as well as comfortable compression above and below the joint. Another benefit of this system is that the brace frame (FIGS. 2A-2E) could contain height adjustment for a short, regular and tall patient. The Y strap shown could also be a simple (single) dynamic force strap without the additional Y strap component. A similar Y strap configuration may also be applied to the lower section of the dynamic offloading strap, without the thigh strap component or in conjunction with the thigh component. When both straps were to be used with the offloading straps, rotational control applied to both thigh and calf can be accomplished. The two additional straps would both anchor to the offloading straps close to knee center however would not have to be anchored at the same location, hence no double crossing in the popliteal would occur. This would allow for optimal placement of such straps without them having to cross in the popliteal which is a common issue for a so called double dynamic force strap brace. The lower strap section would then go through, for example, a D ring on the calf shell for tightening or adjustment by the patient similar to how the dynamic offloading strap is adjusted.

Figure 2A:
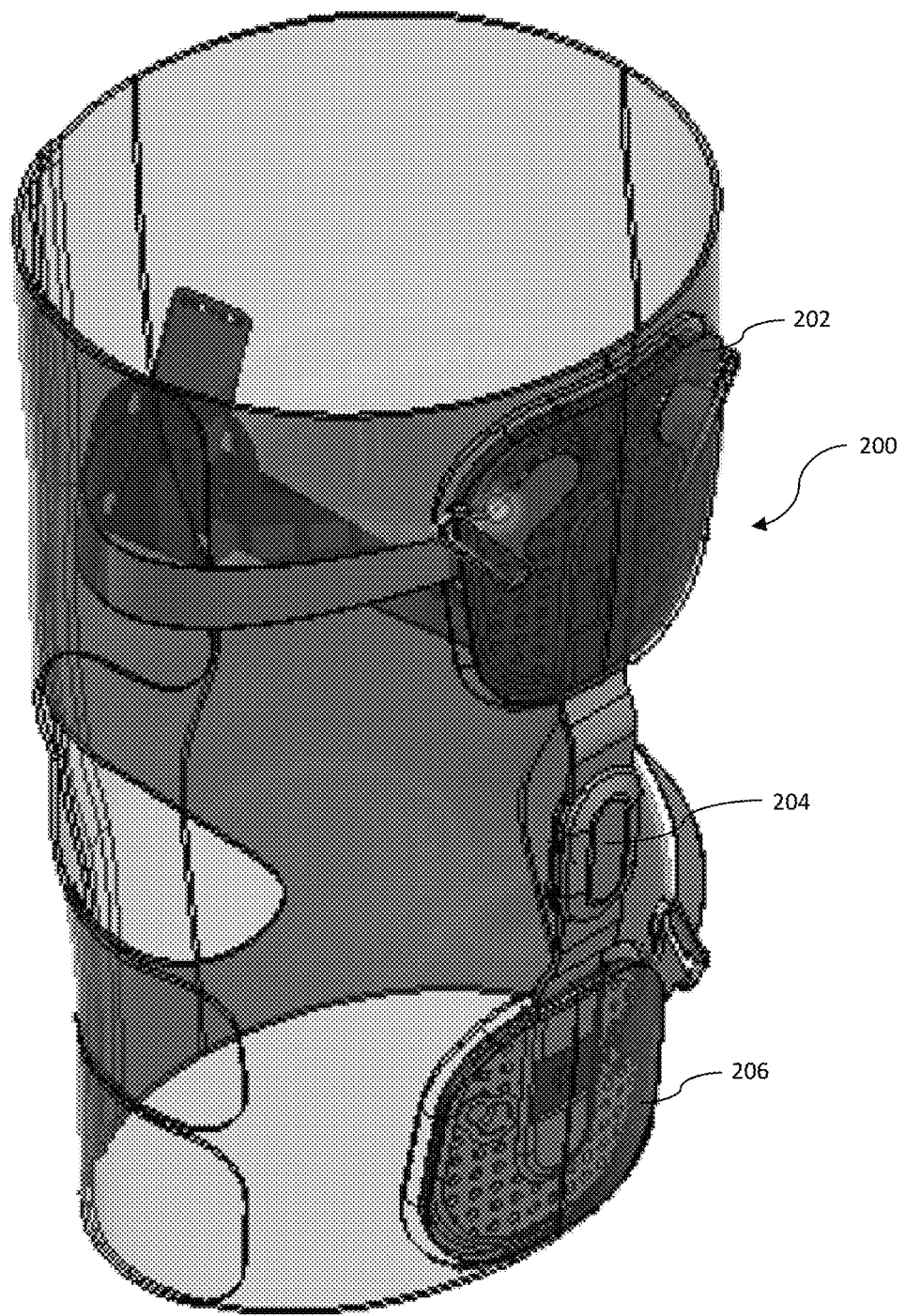
FIG. 2A is a perspective view of an exemplary frame assembly utilized in conjunction with, for example, the orthopedic device(s) illustrated in FIGS. 1A-1I, in accordance with the principles of the present disclosure.
Figure 2B:
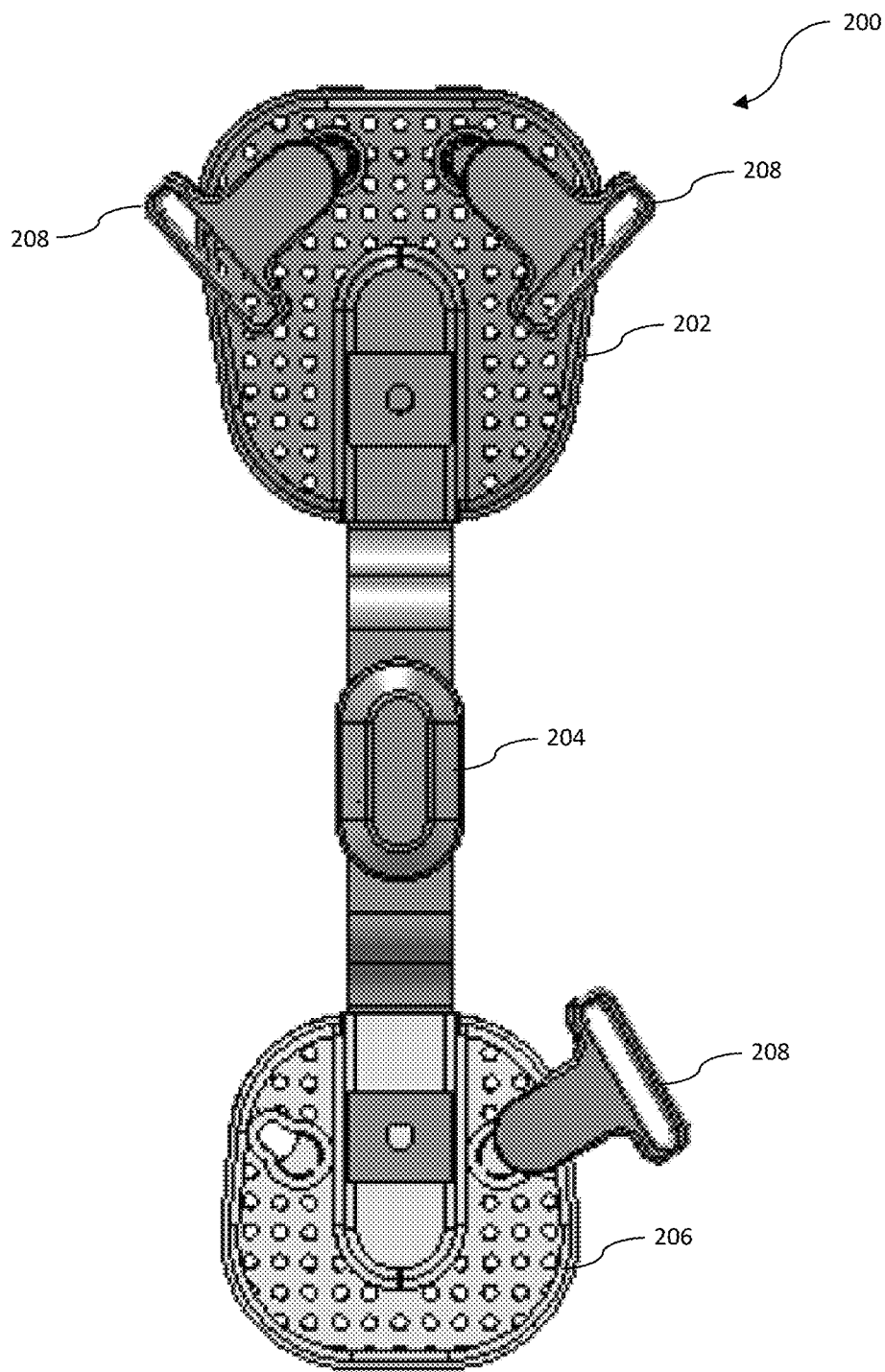
FIG. 2B is a front plan view of the frame assembly illustrated in FIG. 2A, in accordance with the principles of the present disclosure.
Figure 2C:
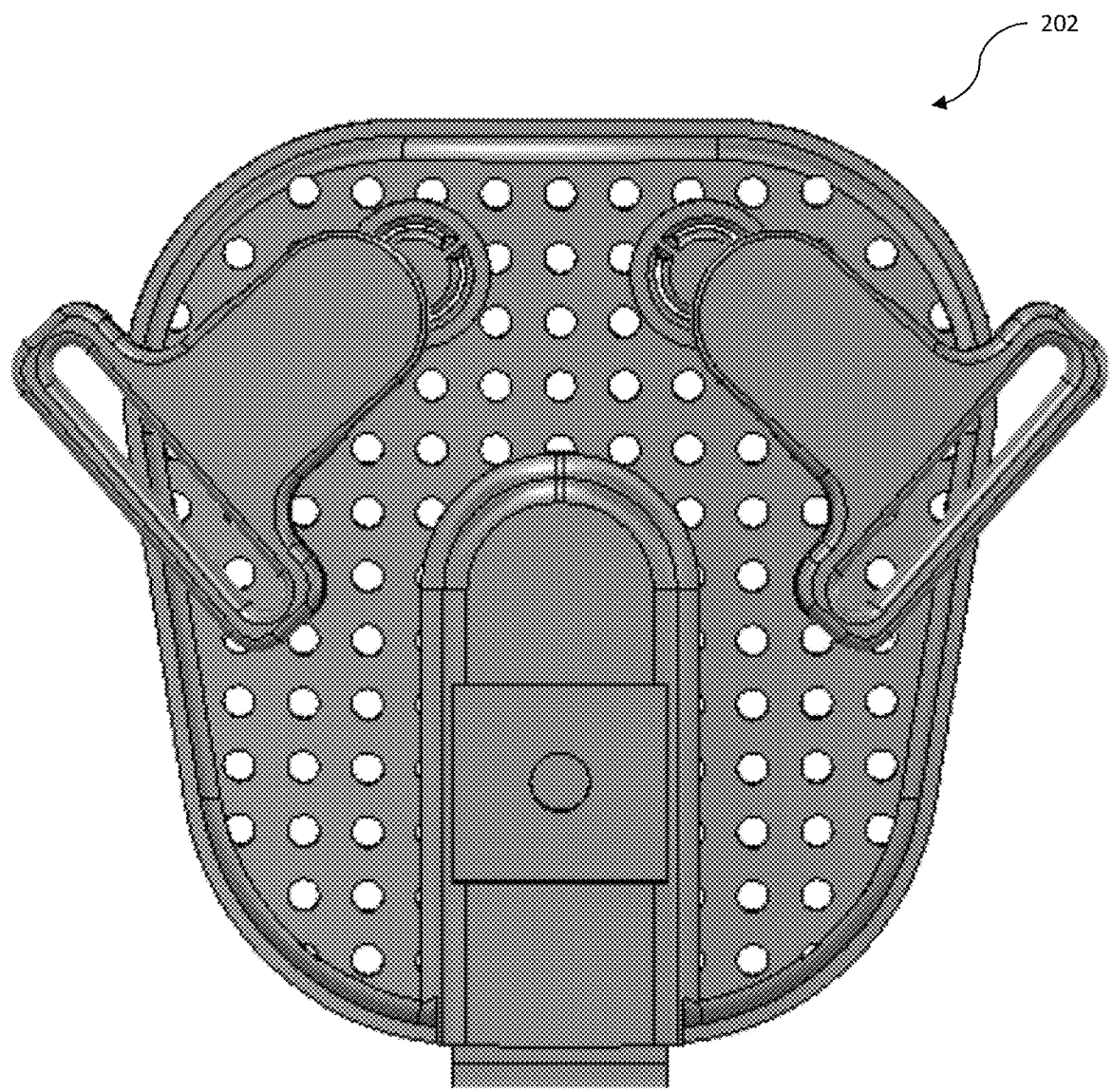
FIG. 2C is a front plan view of the upper part of the frame assembly illustrated in FIG. 2B, in accordance with the principles of the present disclosure.
Figure 2D:
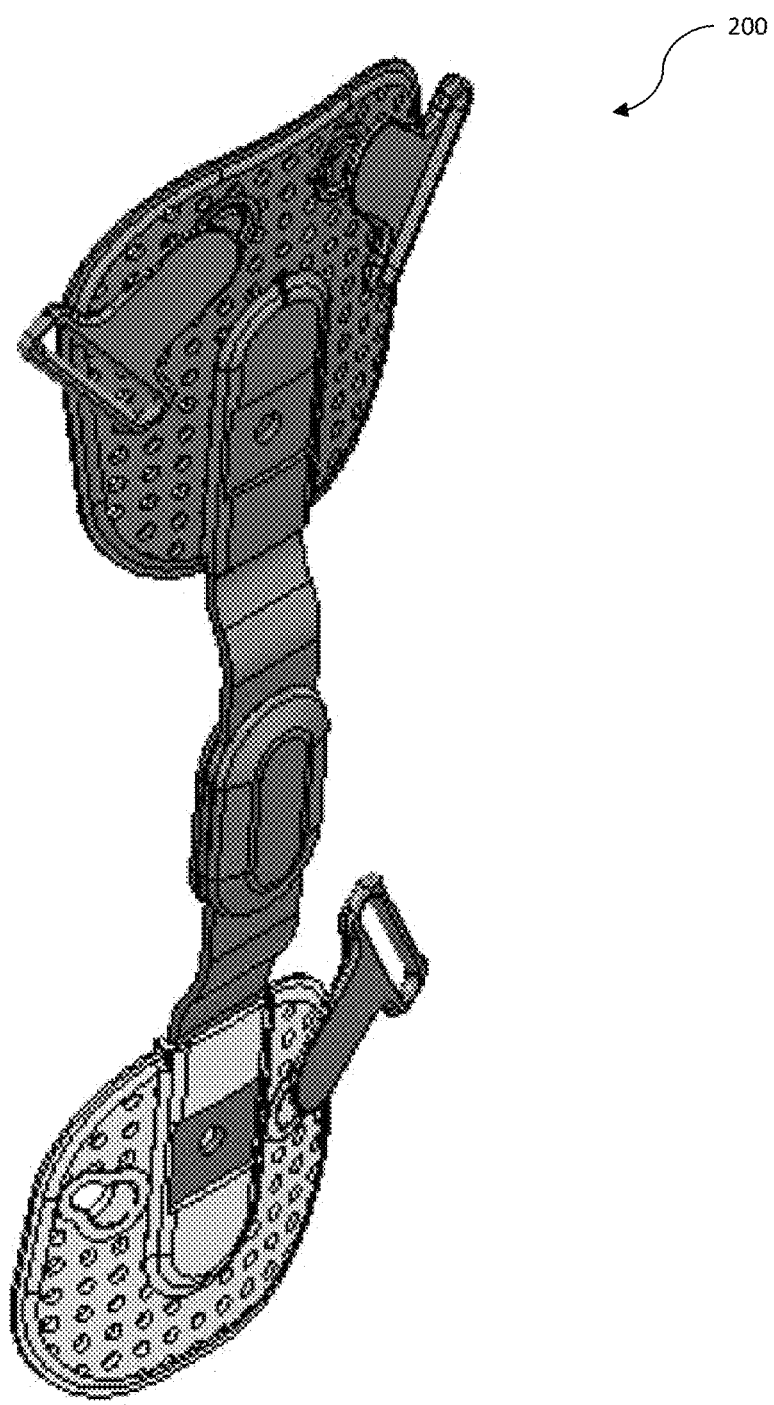
FIG. 2D is a perspective view of the frame assembly illustrated in FIG. 2B, in accordance with the principles of the present disclosure.
Figure 2E:
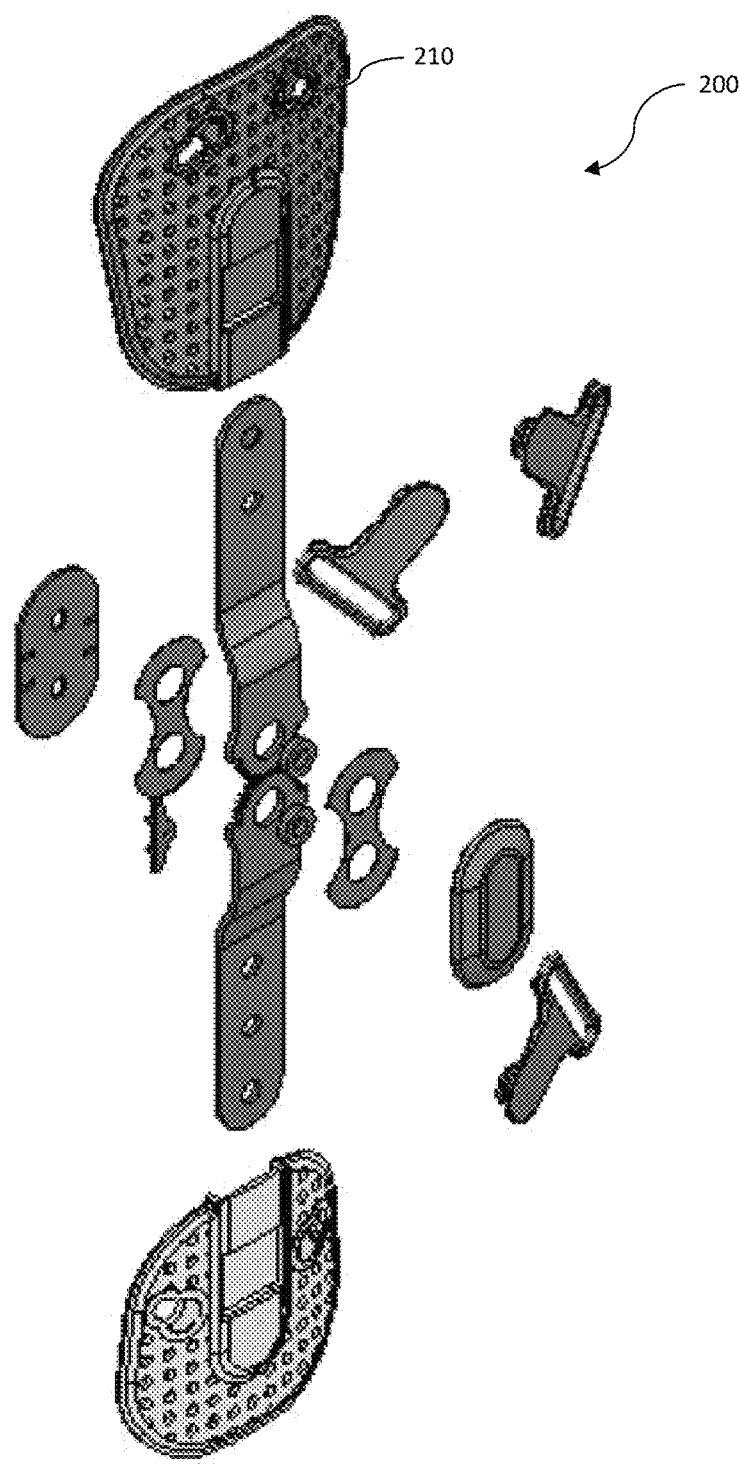
FIG. 2E is an exploded perspective view of the frame assembly illustrated in FIG. 2B, in accordance with the principles of the present disclosure.

FIGS. 2A-2E illustrate an exemplary hinge assembly 200 for use with, for example, the orthopedic device illustrated in FIGS. 1A-1I 3A-3B and 4A-4B. The hinge assembly 200 includes an upper thigh plate 202, a lower calve plate 206 that are each coupled to a hinge 204. Mechanisms located on, for example, the upper thigh plate 202 and the lower calve plate 206 may enable the distance between the two plates 202, 206 to be lengthened or shortened, depending upon the geometry of a wearer of the OA sleeve (and hinge assembly 200). In some implementations, the upper thigh plate 202 will include two anchor locations 208 (e.g., D-rings), while the lower calve plate 206 will include a single anchor location 208. The upper thigh plate 202 anchor locations 208 may be utilized for the dynamic force strap 102, 302 and strap 118, 318. The lower calve plate 206 anchor location 208 may be utilized for the dynamic force strap 102, 302 as well. FIG. 2E illustrates an exemplary exploded view for the hinge assembly 200 illustrating how the hinge assembly 200 is constructed.

Figure 3A:
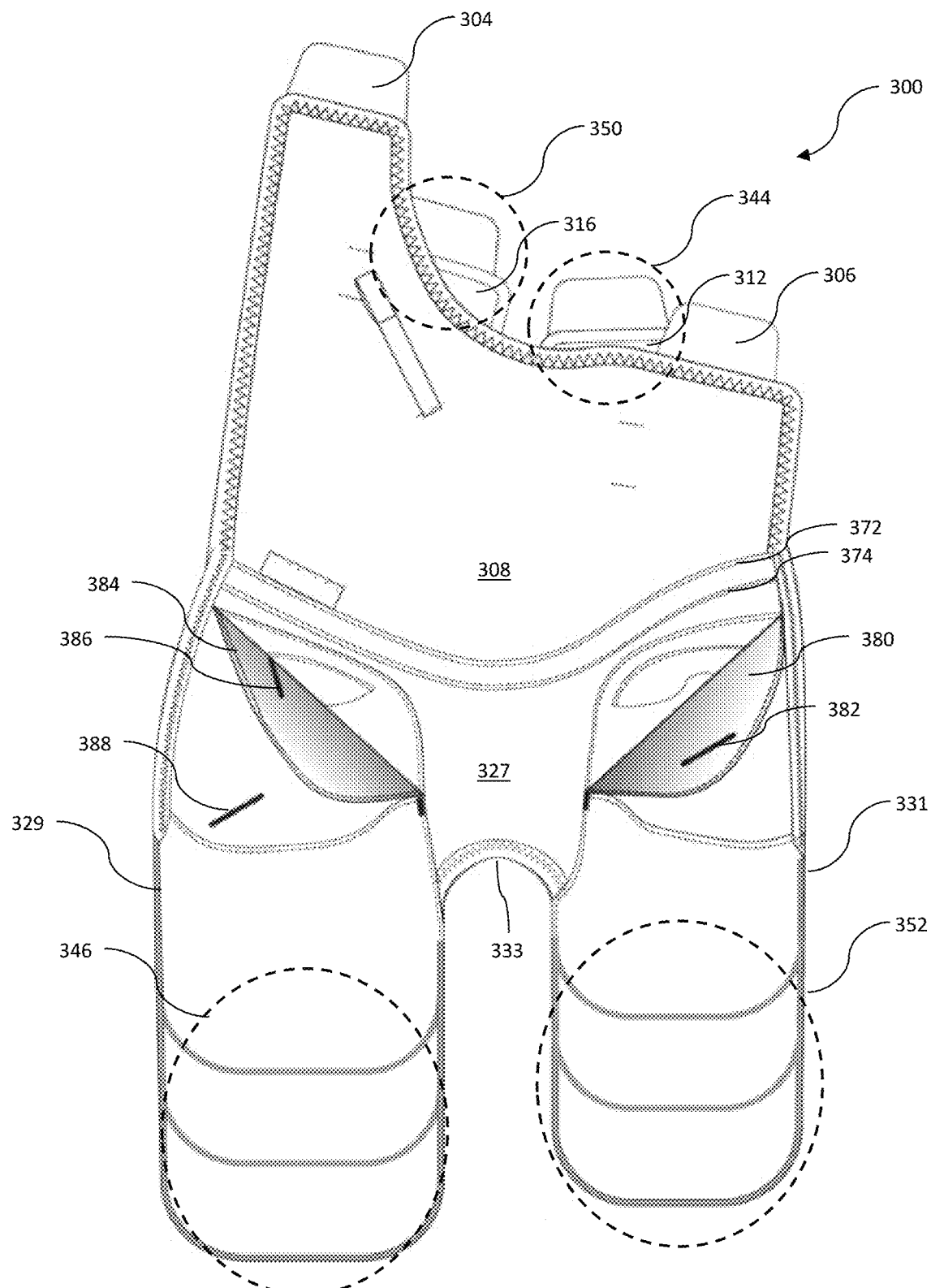
FIG. 3A is a flat view perspective of yet another sleeve configuration used in the Y Unloading strap orthoses, in accordance with the principles of the present disclosure.
Figure 3B:
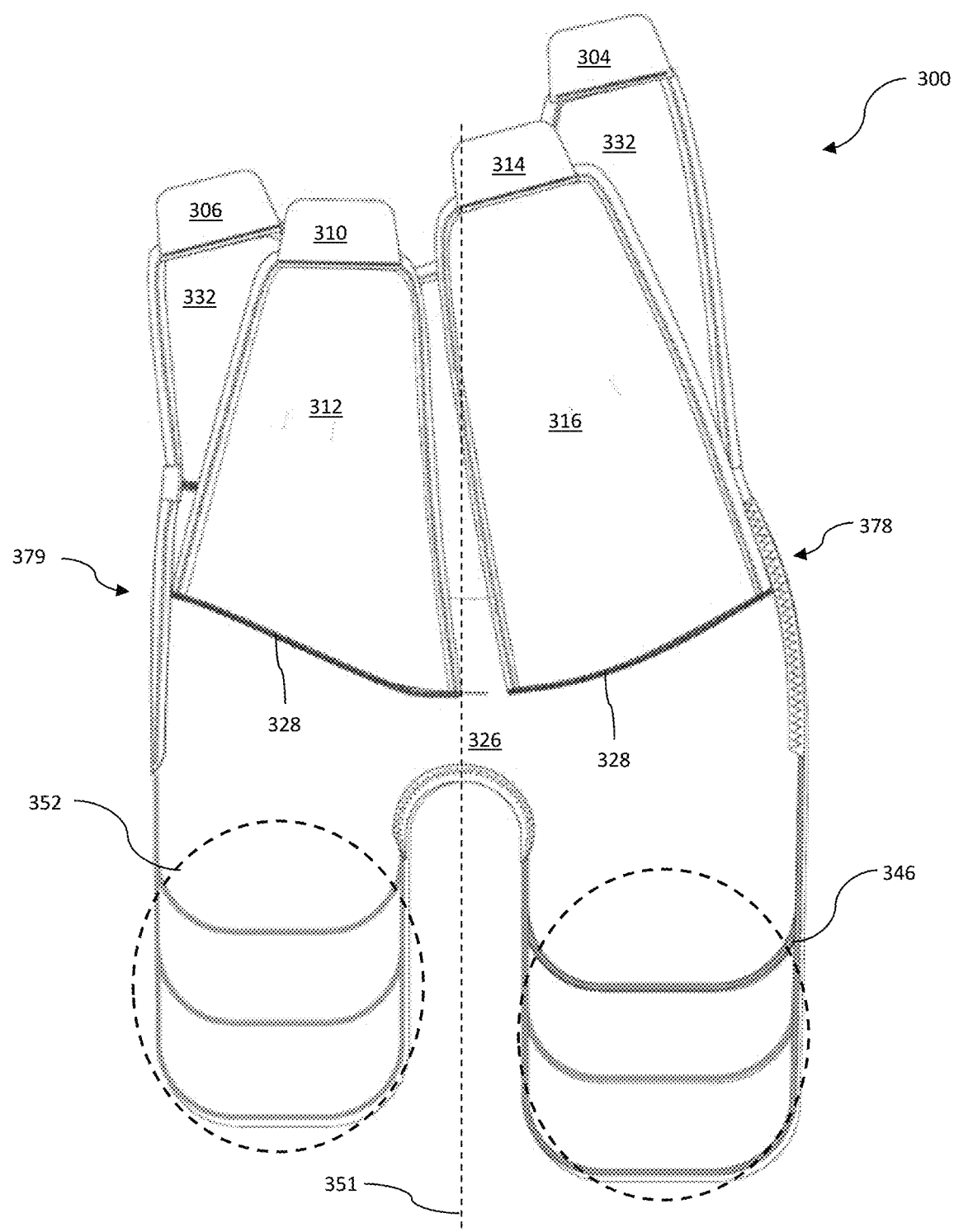
FIG. 3B is a flat view perspective of the configuration of FIG. 3A shown from the opposite side, in accordance with the principles of the present disclosure.

FIGS. 3A and 3B illustrate yet another wraparound sleeve configuration that includes, for example, four attachments. In some implementations, this sleeve configuration may be colloquially referred to as a soft OA brace. In the configuration illustrated in FIG. 3A (an outer flat view), the user may start by applying two straps, one above the calf and one on the lower thigh. The patient may apply a wide panel that includes the bottom calf attachment 306 and the top thigh attachment 304. These two straps 304, 306 sit underneath the wide outer panel 308. Prior to donning the brace, the user (or fitter) may use predetermined trim lines 346, 352 shown in order to adjust the brace to the appropriate circumference size for both thigh and calf. Another circumference adjustment may be made through, for example, the application of one or more wide alligator clips that can be added onto flap to, for example, lengthen brace circumference. As is illustrated in FIG. 3A, the circumference of a user's lower extremities would be positioned in the horizontal direction with the sleeve 300 illustrated as shown in FIG. 3A. The upper panel 308 may be secured to the lower panel 327 via one or more seams 372, 374. The lower panel 327 also includes a first portion 329 that extends away from the upper panel 308 and a second portion 331 that also extends away from the upper panel 308. The first portion 329 and the second portion 331 being separated from one other by a gap defined by a separation feature 333. In the illustrated embodiment, the separation feature 333 comprises a curved edge, although it is appreciated that this separation feature can extend in a straight line across the gap, or may even take on other angular geometries.

The user (or fitter) may also alter the height of the brace (200, FIGS. 2A-2E) by, for example, pushing buttons on thigh shell and calf shell that engage with arms on the hinge to lengthen or shorten the frame by pulling the shells away from the hinge center or pushing the shells towards the hinge center. The sleeve 300 may have sufficient vertical (horizontal direction as depicted in FIG. 3A) elasticity to accommodate the different frame lengths for the brace (200, FIGS. 2A-2E). FIG. 3A also illustrates two pockets 384, 380 that are configured to accommodate the upper thigh plate (202, FIG. 2B) and lower calve plate (206, FIG. 2B), respectively. One of the pockets 384 may include two slots 386, 388 to accommodate the D-rings (208, FIG. 2B) shown on the upper thigh plate (202, FIG. 2B), while the other pocket 380 may include a slot 382 to accommodate the D-ring (208, FIG. 2B) shown on the lower calve plate (206, FIG. 2B).

These pockets 380, 384 may be configured to attach to the lower panel 327 via the user of a variety of the means including, without limitation, Velcro®, zippers, buttons, clasps, or literally any other attachment means. By enabling the pockets 380, 384 to be removably opened (or closed), the hinge assembly (200, FIGS. 2A-2E) can be, for example, selectively removable from the sleeve 300, thereby enabling the ability for the sleeve to be cleaned (e.g., with a washing machine, hand wash, or similar).

FIG. 3B shows the inner flat view of the orthopedic device 300 shown in FIG. 3A. The first strap 312 preferably extends from a first seam 328 that is located on the first panel 326. Notably, the seam 328 is located away from the seam line(s) between the upper 332 and lower 326 panels. The first strap 312 also is narrower in width as the panel 312 runs from the seam 328 toward the flap (strap) 310. The first strap 312 also runs generally parallel with the centerline 351 of the orthopedic device 300. One exemplary benefit of this disclosed configuration is for suspension. Namely, strap 312 may be the most important of the straps for suspension and may be, for example, the first one of the straps that is applied in order to make sure that the brace stays on the leg well during donning. The seam 328 may define a profile with at least one curved segment, and the first strap 312 is secured along the curved segment of the seam 328.

A second strap 316 extends above its own unique seam 328, as compared with the seam associated with the first strap 312. Again, notably the seam 328 for the second strap 316 is also located away from the seam line(s) between the upper 332 and lower 326 panels. The second strap 316 also is slightly narrower in width as the panel 316 runs from the seam 328 toward the flap (strap) 314. The second strap 316 also runs generally towards the centerline 351 of the orthopedic device 300 from the seam 328 towards the flap (strap) 314. The second strap 316 may have a longer length than a length of the first strap 312.

Lying behind these first 312 and second straps 316, is a second panel 332. The second panel 332 preferably defines at least one flap 304 located on one end 378 of the orthopedic device. The portion of the panel 332 associated with the flap 304 also generally runs toward the centerline of the orthopedic device 300. On the opposing end 379 of the device 300, a second flap 306 may also be included which runs generally away from the centerline 351 of the orthopedic device 300. Collectively, flaps 304, 306 are both attached to a common panel 332 (see also panel 308, FIG. 3A); however, it is appreciated that they may be separated from one another in some implementations. For example, the two flaps 304, 306 may be spaced apart by a gap so that a patella opening is formed in combination with the second side of the first panel. However, by sharing a common panel, it may assist a user in donning the device 300 by making placement easier as compared with an implementation that includes separate flaps 304, 306. The flaps 304, 306, 310, 314 may include fastener material for engaging corresponding fastener material (e.g., Velcro®) located on the opposing side of the first panel 326.

An exemplary usage scenario for some implementations of the flaps (straps) 304, 314, 310, 306 depicted in FIGS. 3A-3B is now described. The combination of straps 312, 316 and panel 332 serves to contain the soft tissue around the knee of the wearer and to hold the orthopedic device 300 on the leg of the wearer. Flap 304 may connect to the top portion of the second panel 332 and therefore constitutes the top strap (i.e., the strap positioned on the thigh of the wearer). Flap 314 may connect to the second strap 316 from the top. Flap 310 may connect to the first strap 312 which is the second from the bottom and flap 306 may connect to the bottom portion of the second panel 332 and therefore constitutes the bottom strap. Straps 312 and 316 are separate straps and flaps 304 and 306 are connected to a separate panel for straps 312 and 316.

Figure 3C:
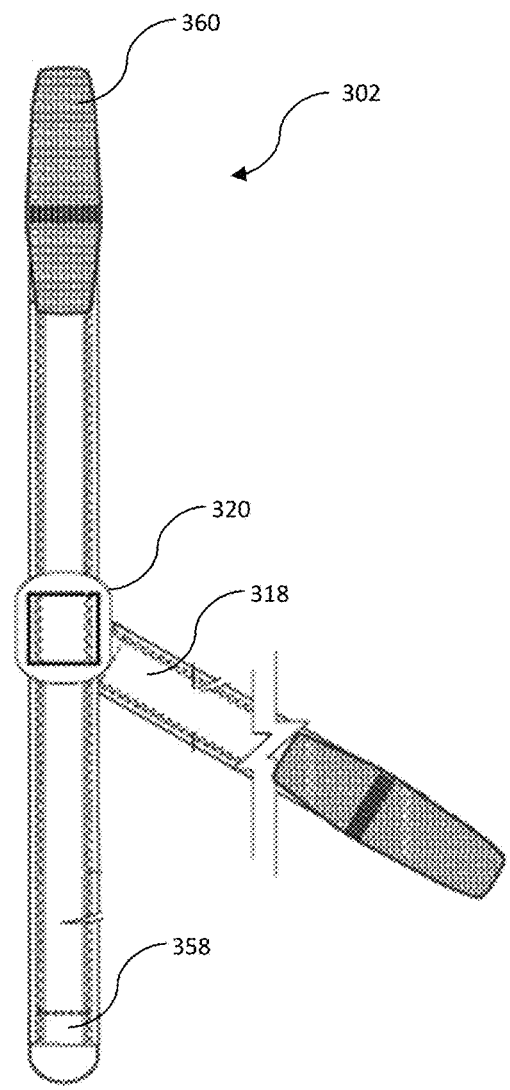
FIG. 3C is a flat view perspective of another embodiment of a dynamic force strap for use with, inter alia, the sleeve configuration shown in FIGS. 3A and 3B, in accordance with the principles of the present disclosure.
Figure 3D:
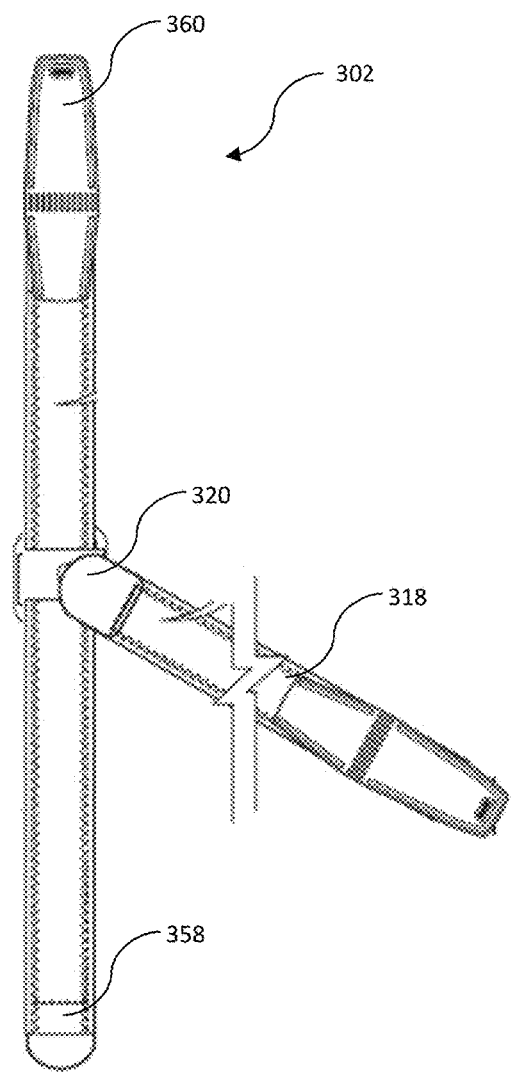
FIG. 3D is a flat view perspective of the configuration of FIG. 3C shown from the opposite side, in accordance with the principles of the present disclosure.

FIGS. 3C and 3D illustrate the dynamic force strap 302 for use with, for example, the hinge assembly (200, FIGS. 2A-2E). In particular, FIG. 3C illustrates the other side of the dynamic force strap shown in FIG. 3D. They dynamic force strap 302 is configured to helically extend between, for example, upper and lower portions of the orthopedic device 300. The second force strap 318 connects to a middle portion of the dynamic force strap 302 via, for example, a buckle or slide 320, travels up the leg, opposite of the dynamic force strap 102 and connects to, for example, the upper thigh plate (202, FIG. 2B), opposite of the dynamic force strap end 358. The dynamic force strap 302 has first 358 and second ends 360 for securing to the upper thigh plate (202, FIG. 2B) and lower calve plate (206, FIG. 2B) of the hinge assembly (200, FIGS. 2A-2E). The buckle or slide 320 enables the dynamic force strap 302 to be adjusted easily to a given user's anatomy. In some implementation, the top portion of the fabric illustrated in FIG. 3C may be a woven fabric, while the top portion of the fabric illustrated in FIG. 3D may be a knitted loop fabric. As a brief aside, a knit fabric is typically made from a single yarn that is looped continuously in order to produce a braided look to the fabric, while a woven fabric is made of multiple yarns that cross each other at, for example, right angles so as to produce a different look and feel. In other implementations, the knitted loop and woven fabric may be switched, or even replaced with a unitary construction (e.g., either knitted loop or woven fabric) in some implementations. These and other variants would be readily apparent to one of ordinary skill given the contents of the present disclosure.

Figure 4A:
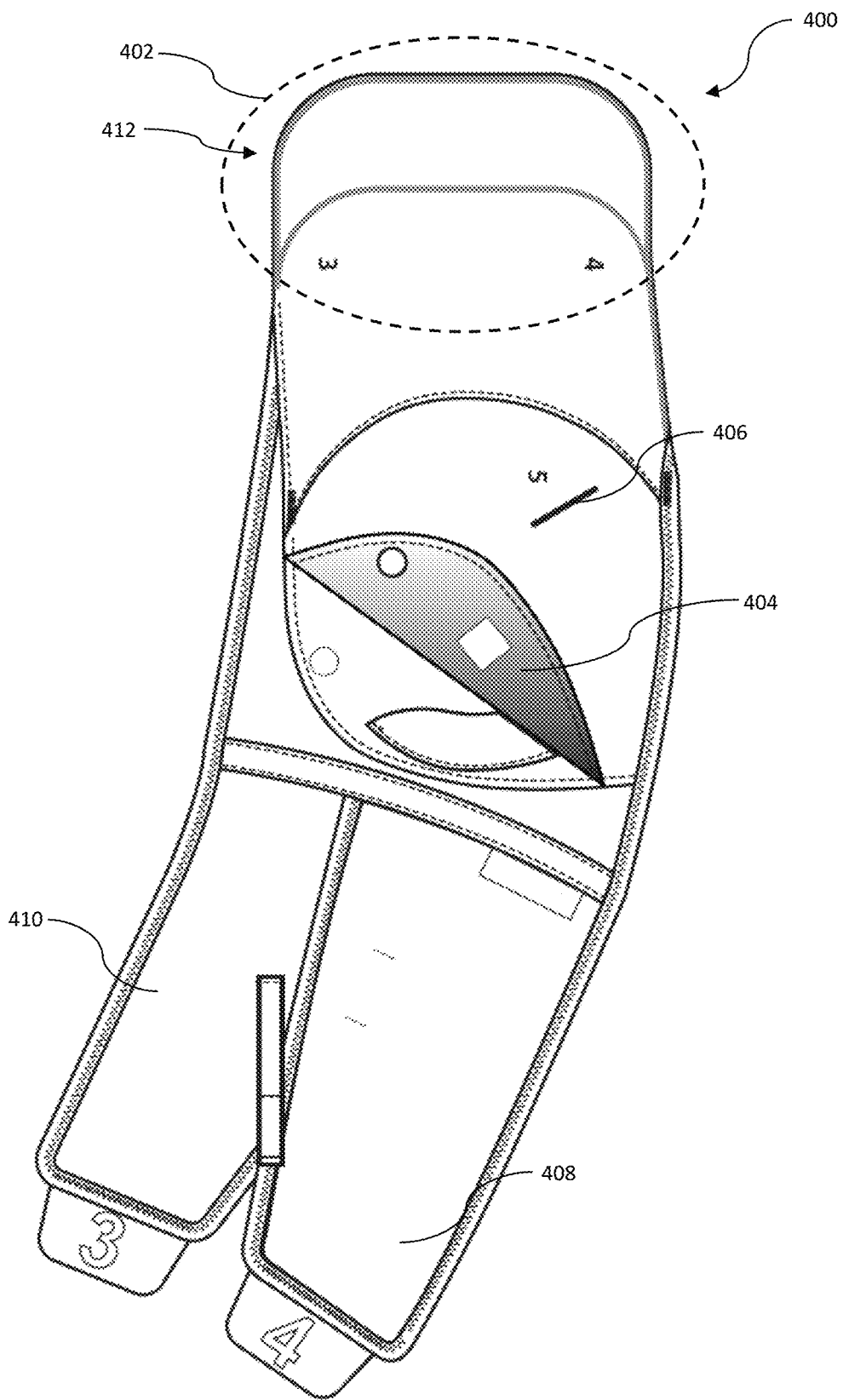
FIG. 4A is a flat view perspective of a thigh wrap for an orthopedic device, in accordance with the principles of the present disclosure.
Figure 4B:
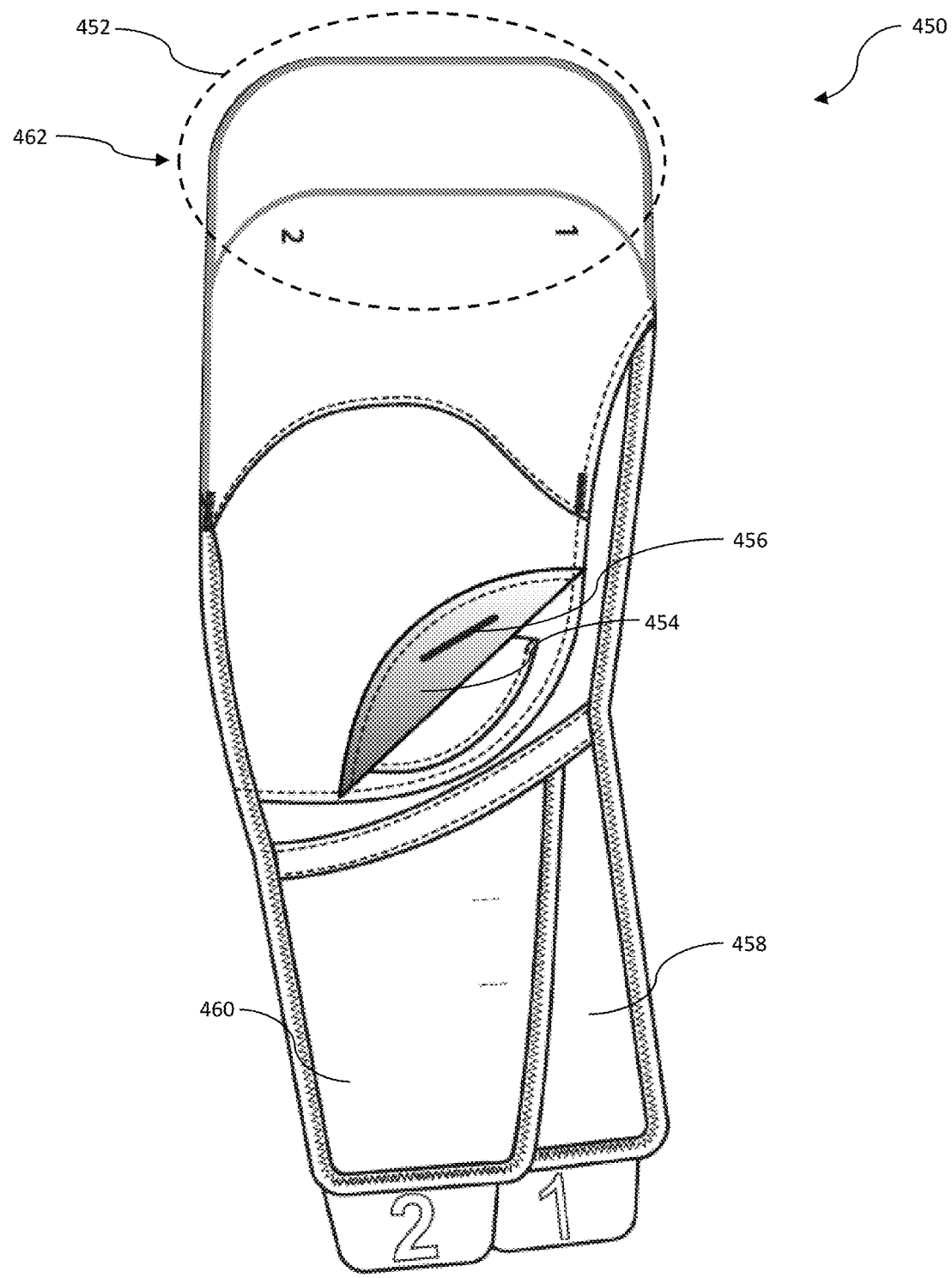
FIG. 4B is a flat view perspective of a calve wrap for an orthopedic device for use with the thigh wrap of FIG. 4A, in accordance with the principles of the present disclosure.

Referring now to FIGS. 4A-4B, yet another configuration for an orthopedic device (e.g., an OA brace) is shown and described in detail. Specifically, FIG. 4A illustrates a thigh wrap 400 for the orthopedic device, while FIG. 4B illustrates a calve wrap 450 for the orthopedic device. Prior to donning the wraps 400, 450, the user (or fitter) may use the predetermined trim lines 402, 452 shown in order to adjust the brace to the appropriate circumference size for both thigh and calf. Another circumference adjustment may be made through, for example, the application of one or more wide alligator clips that can be added onto flap to, for example, lengthen brace circumference. FIGS. 4A-4B also illustrates two pockets 404, 454 that are configured to accommodate the upper thigh plate (202, FIG. 2B) and lower calve plate (206, FIG. 2B), respectively.

One of the pockets 404 may include two slots 406 to accommodate the b-rings (208, FIG. 2B) shown on the upper thigh plate (202, FIG. 2B), while the other pocket 454 may include a slot 456 to accommodate the D-ring (208, FIG. 2B) shown on the lower calve plate (206, FIG. 2B). These pockets 404, 454 may be configured to attach to the panel of the wrap via the user of a variety of the means including, without limitation, Velcro®, zippers, buttons, clasps, or literally any other attachment means. By enabling the pockets 404, 454 to be removably opened (or closed), the hinge assembly (200, FIGS. 2A-2E) can be, for example, selectively removable from the wraps 400, 450, thereby enabling the ability for the wraps to be cleaned (e.g., with a washing machine, hand wash, or similar). Wrap 400 includes to straps 408, 410 which are configured to be attached to the other end 412 of the wrap 400, while wrap 450 also includes two straps 458, 460 which are configured to be attached to the other end 462 of wrap 450. Collectively, these wraps are intended to be placed around the upper and lower leg of a user separately in a fashion similar to that shown in the embodiment of FIG. 1I.

Where certain elements of these implementations can be partially or fully implemented using known components, only those portions of such known components that are necessary for an understanding of the present disclosure are described, and detailed descriptions of other portions of such known components are omitted so as not to obscure the disclosure.

In the present specification, an implementation showing a singular component should not be considered limiting; rather, the disclosure is intended to encompass other implementations including a plurality of the same component, and vice-versa, unless explicitly stated otherwise herein.

Further, the present disclosure encompasses present and future known equivalents to the components referred to herein by way of illustration.

It will be recognized that while certain aspects of the technology are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed implementations, or the order of performance of two or more steps permuted. All such variations are considered to be encompassed within the disclosure disclosed and claimed herein.

While the above detailed description has shown, described, and pointed out novel features of the disclosure as applied to various implementations, it will be understood that various omissions, substitutions, and changes in the form and details of the device or process illustrated may be made by those skilled in the art without departing from the disclosure. The foregoing description is of the best mode presently contemplated of carrying out the principles of the disclosure. This description is in no way meant to be limiting, but rather should be taken as illustrative of the general principles of the technology. The scope of the disclosure should be determined with reference to the claims.

What is claimed:

1. An orthopedic device, comprising:
  a first panel defining opposed first and second sides;
  a second panel having a first end secured to the first side of the first panel along a seam, and a second end securable to the second side of the first panel at a location site;
  a first strap having a first end secured to the first side of the first panel along the seam and laying under the second panel, and a second end securable to the second side of the first panel at the location site;
  a second strap having a first end secured to the first side of the first panel along the seam and laying under the second panel, and a second end securable to the second side of the first panel at the location site;
  a dynamic force strap helically extending between upper and lower portions of the orthopedic device and connecting to the first panel; and
  a second dynamic force strap comprising a first end and a second end, the first end of the second dynamic force strap attached to a center of the dynamic force strap and the second end of the second dynamic force strap attached to the first panel opposite where the dynamic force strap connects to the first panel, wherein the second dynamic force strap extends helically from the center of the dynamic force strap, connects to the first panel, and terminates at the center of the dynamic force strap and the first panel.

2. The orthopedic device of claim 1, further comprising a hinge assembly secured to the first panel and extending between upper and lower portions of the orthopedic device.

3. An orthopedic device, comprising:
  a soft good attached to a thigh shell comprising a first panel defining opposed first and second sides;
  a second panel having a first end secured to the first side of the first panel along a seam between upper and lower corners of the seam, and a second end defining at least one flap securable to the second side of the first panel at a location site;
  a first strap having a first end secured to the first side of the first panel and extending from an upper portion of the seam including the upper corner of the seam and overlying at least a portion of the second panel, and a second end securable to the second side of the first panel at the location site;
  a dynamic force strap helically extending between upper and lower portions of the orthopedic device and connecting to the first panel;
  a second dynamic force strap comprising a first end and a second end, the first end of the second dynamic force strap attached to a center of the dynamic force strap and the second end of the second dynamic force strap attached to the first panel opposite where the dynamic force strap connects to the first panel, wherein the second dynamic force strap extends helically from the center of the dynamic force strap, connects to the first panel, and terminates at the center of the dynamic force strap and the first panel;
  a hinge assembly secured and slidable in relation to the thigh shell and a calf shell, the hinge assembly secured to the first panel and extending between upper and lower portions of the orthopedic device.

4. The orthopedic device of claim 3, wherein the slidable relation works in conjunction with a push button.

5. The orthopedic device of claim 4, wherein at least one of the thigh shell and the calf shell comprise keyholes for attachment of D rings and straps;
  wherein the dynamic force strap has first and second ends securing to the thigh shell and the calf shell spaced apart by first and second struts connected to one another by a hinge;
  and wherein the thigh shell and the calf shell each comprise ventilated shells for breathability.

* * * * *